United States Patent [19]
Dutta

[11] Patent Number: 6,034,057
[45] Date of Patent: Mar. 7, 2000

[54] PEPTIDE INHIBITORS OF FIBRONECTINE

[75] Inventor: Anand Swaroop Dutta, Macclesfield, United Kingdom

[73] Assignee: Zeneca Limited, London, United Kingdom

[21] Appl. No.: 08/981,680

[22] PCT Filed: Jul. 2, 1996

[86] PCT No.: PCT/GB96/01580

§ 371 Date: Jan. 6, 1998

§ 102(e) Date: Jan. 6, 1998

[87] PCT Pub. No.: WO97/02289

PCT Pub. Date: Jan. 23, 1997

[30] Foreign Application Priority Data

Jul. 6, 1995 [GB] United Kingdom .................... 9513798
Jun. 1, 1996 [GB] United Kingdom .................... 9611470

[51] Int. Cl.$^7$ .............................. A41K 38/12; C07K 5/12
[52] U.S. Cl. .................... 514/9; 514/11; 514/16; 530/317; 530/328
[58] Field of Search .................... 530/317, 328; 514/9, 11, 16

[56] References Cited

U.S. PATENT DOCUMENTS 5,229,366 7/1993 Tsukuda et al. ........................... 514/12
5,510,332 4/1996 Kogan et al. .............................. 514/11

FOREIGN PATENT DOCUMENTS

| 0341915 | 11/1989 | European Pat. Off. |
| 0422938 | 4/1991 | European Pat. Off. |
| WO 92/00995 | 1/1992 | WIPO |
| 94/02445 | 2/1994 | WIPO |
| 94/15958 | 7/1994 | WIPO |
| 95/14714 | 6/1995 | WIPO |
| 95/15973 | 6/1995 | WIPO |
| 96/00581 | 1/1996 | WIPO |
| 96/06108 | 2/1996 | WIPO |
| 96/20216 | 7/1996 | WIPO |
| 97/02289 | 1/1997 | WIPO |

OTHER PUBLICATIONS

Wayner: "Activation–dependent recognition by hematopoietic cells of the LDV sequence in the V region of fibronectin", Journal of Cell Biology, bol. 116, No. 2, 1991, pp. 489–497, cited in the application, see the whole document.
Kiso: "Synthesis of ANP fragments with hypertensive action", Chemical Abstracts, vol. 110, No. 3, Jan. 16, 1989; abstract No. 24283k, p. 592, col. 1; see abstract & Pept. Chem.,–1987 pp. 512–516.
B. Weinstein; "Chemistry and Biochemistry of Amino Acids, Peptides and Proteins", 1983, See p. 338–p.341.
Aumailley et al., "Arg–Gly=Asp constrained within cyclic pentapeptides—Strong and selective inhibitors of cell adhesion of vitronectin and laminin fragment P1", Federation of European Biochemical Societies, Oct., 1991, pp. 50–54.
Lublin, "Susceptibility to experimental allergic encephalomyelitis in animal models of autoimmunity", Neurology and Neurosurgery, 1992, vol. 5, pp. 182–187.
Bowen et al., "Disease–Modifying Anti–Rheumatic Drugs: Strategies for Screening", Pharmac. Ther. 1992, vol. 56, pp. 287–306.
Nakajima et al., Role of Vascular Cell Adhesion Molecule 1/Very Late Activation Antigen 4 and Intercellular Adhesion Molecule 1/Lymphocyte Function–associated Antigen 1 Interaction in Antigen–induced Eosinophil and T Cell Recruitment into the Tissue. J. Exp. Med. Apr., 1994, pp. 1145–1154.
Pretolani et al., Antibody to Very Late Activation Antigen 4 Prevents Antigen–induced Bronchial Hyperreactivity and Cellular Infiltration in the Guinea Pig Airways, J. Exp. Med., Sep. 1994, pp. 795–805.
Bowen, et al, Pharmac. Ther. vol. 56, pp. 287–306, 1992.

*Primary Examiner*—Bennett Celsa
*Attorney, Agent, or Firm*—Pillsbury Madison & Sutro, LLP

[57] ABSTRACT

Cyclic dimeric peptides of formula (I)

Formula 1

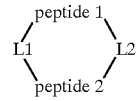

wherein: peptide 1 and peptide 2 independently represent a tetrapeptide of formula -AA1-AA2-AA3-AA4- juxtaposed in parallel or antiparallel orientation; AA1 is an L or D amino acid selected from Ile, Leu and amino analogues thereof selected from Pro, Gly, Tic and Phe; AA2 is an L amino acid selected from Leu and amino acid analogues thereof selected from Ile, Phe and Val; AA3 is an L amino acid selected from Asp, Glu and amino acid analogues thereof; AA4 is an L amino acid selected from Val and amino acid analogues thereof selected from Leu, Ile, Phe and Cha (cyclohexylalanine); L1 and L2 independently represent linking moieties for linking peptides 1 and 2 to form a cyclic dipeptide; or salts thereof. The cyclic dipeptides inhibit the interaction of vascular cell adhesion molecule-1 and fibronectin with integrin very late antigen 4 and have therapeutic applications such as in rheumatoid arthritis, asthma or multiple sclerosis.

16 Claims, 11 Drawing Sheets

Formula 1

Formula 2

Formula 3

Fig.4.
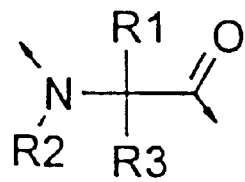
Formula 4
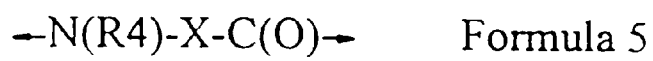
Formula 5
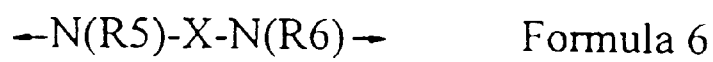
Formula 6
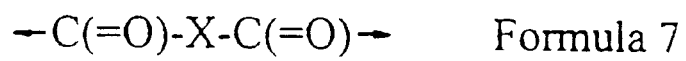
Formula 7
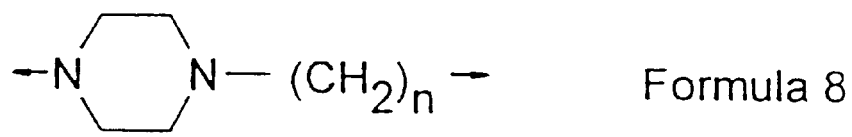
Formula 8
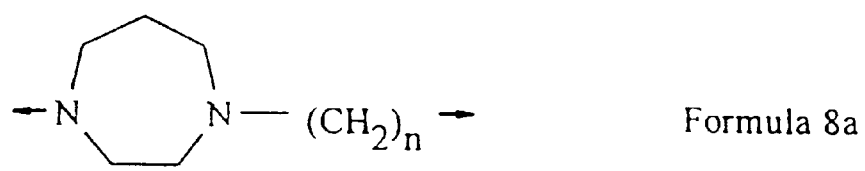
Formula 8a
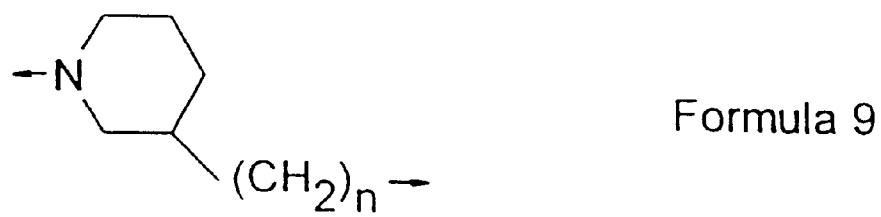
Formula 9

Fig. 5.
Step 1
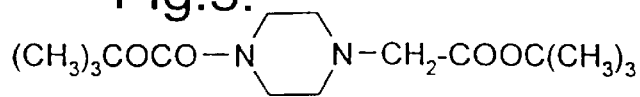
Step 2
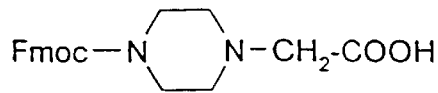
Step 3
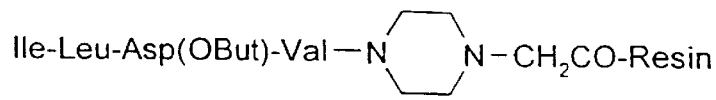
Step 4
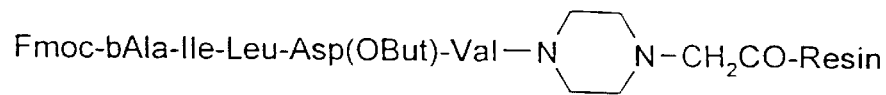
Step 5
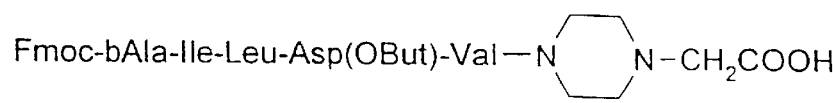
Step 6
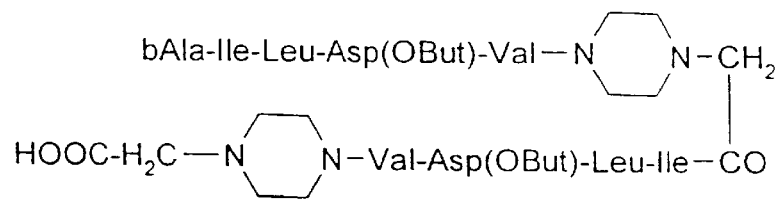
Step 7
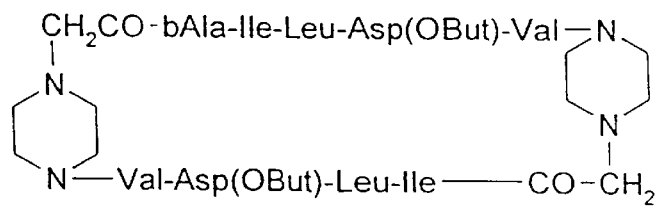
Step 8
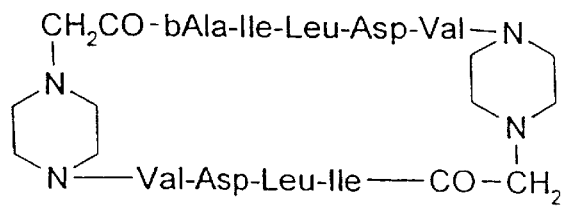

Fig. 6.

Step 1

Fmoc—Val-Chlorotritylresin

Step 2

Asp(OBut)-Val-D-Arg(Pbf)-MeIle-Leu-Asp(OBut)-Val-Chlorotritylresin
|
Leu-MeIle-(Pbf)Arg-D-Fmoc

 Piperidine

Step 3

Asp(OBut)-Val-D-Arg(Pbf)-MeIle-Leu-Asp(OBut)-Val-Chlorotritylresin
|
Leu-MeIle-(Pbf)Arg-D

 Acetic acid/Trifluoroethanol
Dichloromethane

Step 4

D-Arg(Pbf)-MeIle-Leu—Asp(OBut)-Val-D-Arg(Pbf)-MeIle-Leu-Asp(OBut)-Val

 Cyclisation

Step 5 c(D-Arg(Pbf)-MeIle-Leu—Asp(OBut)-Val-D-Arg(Pbf)-MeIle-Leu-Asp(OBut)-Val)

 Trifluoroacetic acid/water/
Triisopropylsilane

Step 6 c(D-Arg-MeIle-Leu—Asp-Val-D-Arg-MeIle—Leu-Asp-Val)

Fig.7.
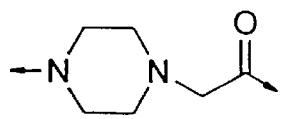
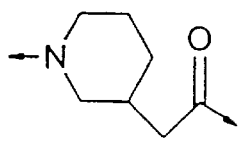
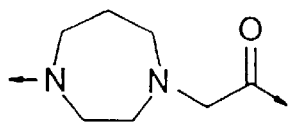
Fig.8.
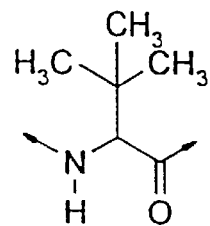
[t-butyl-glycine, t-leucine]
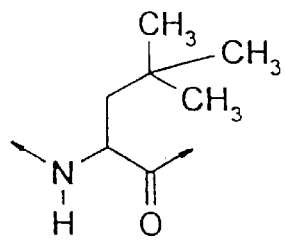
[t-butyl-alanine, neopentylglycine]
Fig.12.
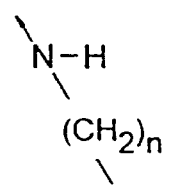 n=1-4 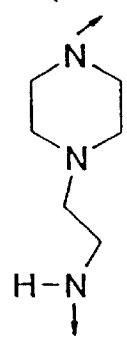
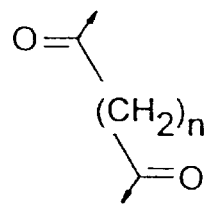
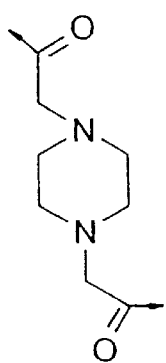

Fig.9.
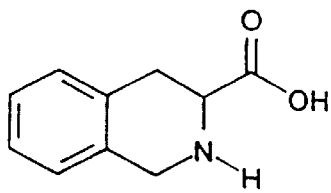
1
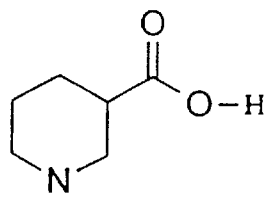
2
Fig.10.
Formula 10
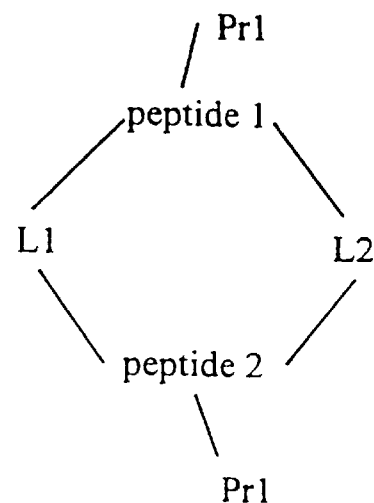
Fig.11.
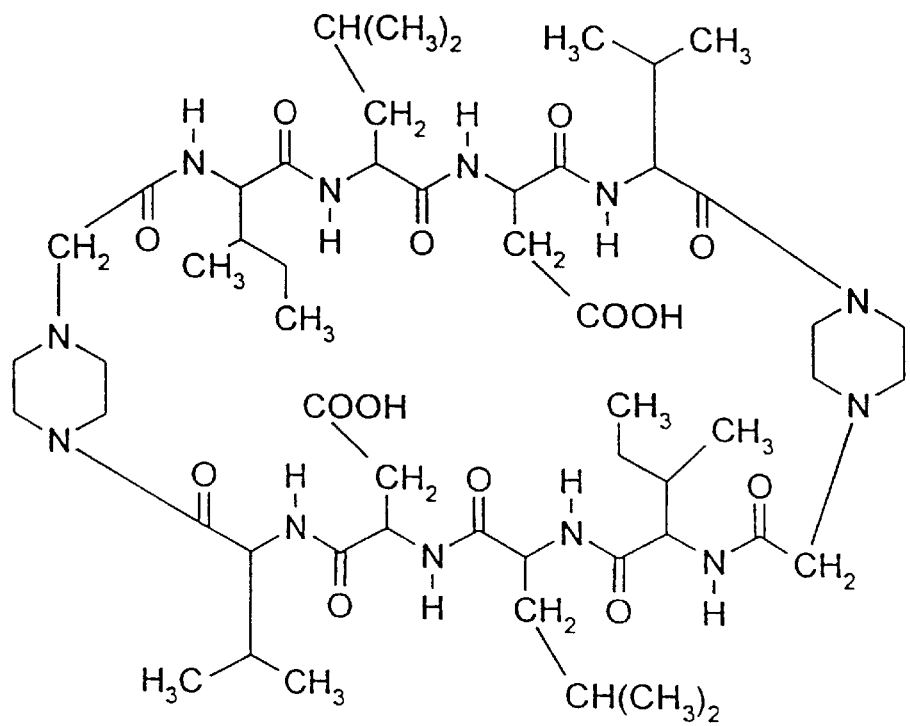

Fig. 14.
Step 1
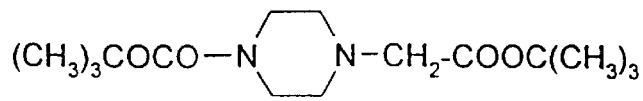
Step 2
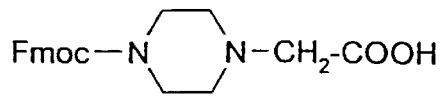
Step 3
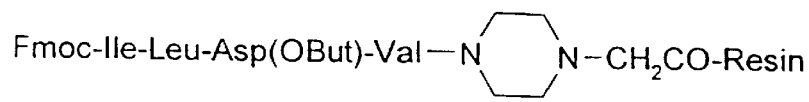
Step 4
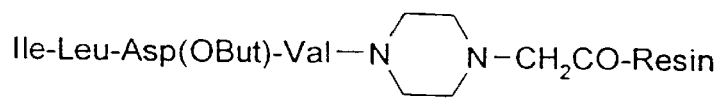
Step 5
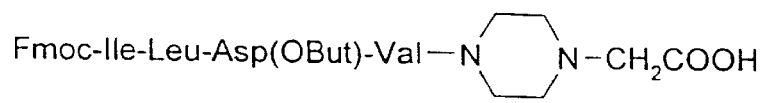
Step 6
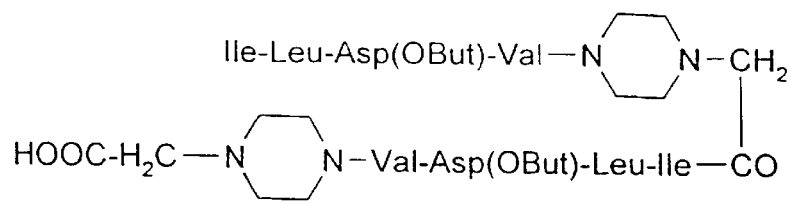
Step 7
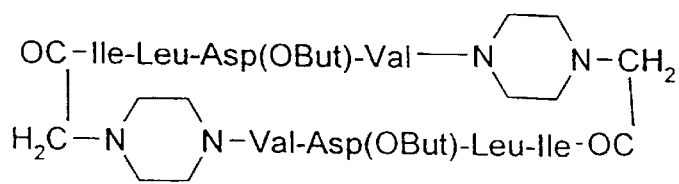
Step 8
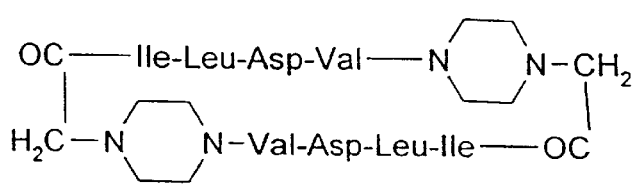

Fig.15.
Step 1
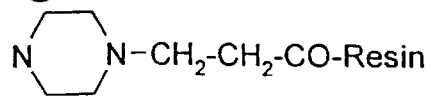
Step 2
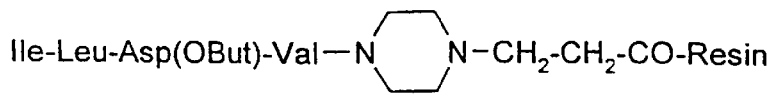
Step 3
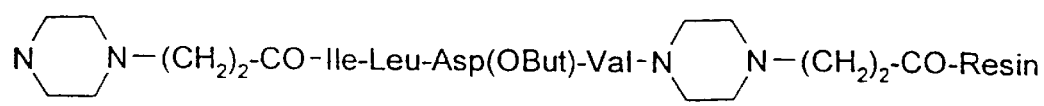
Step 4
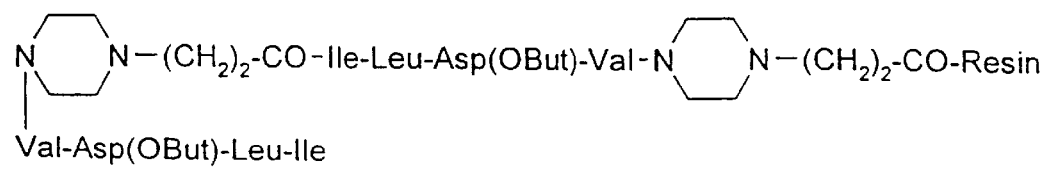
Step 5
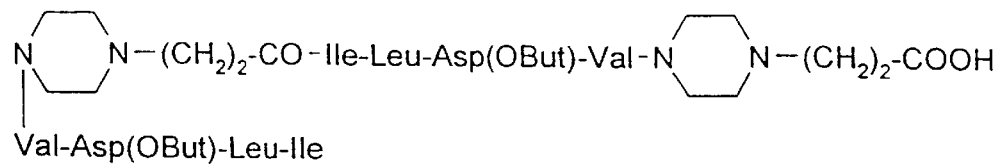
Step 6
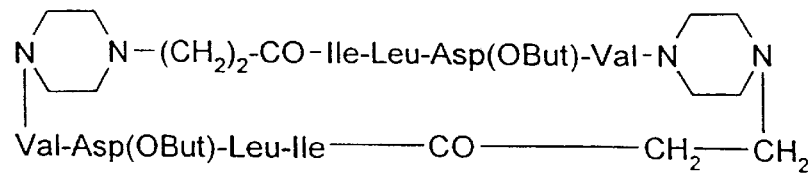
Step 7
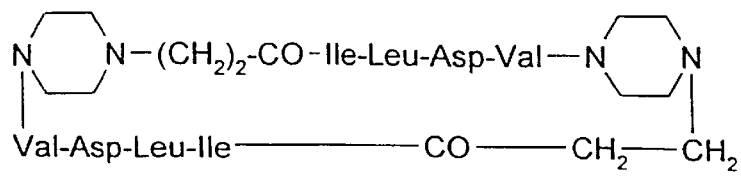

Fig. 16.
Step 1 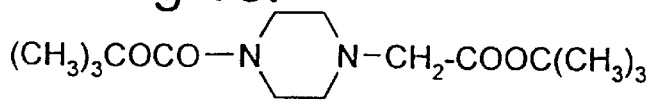
Step 2 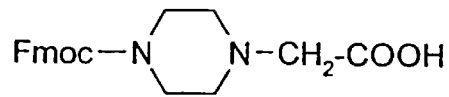
Step 3 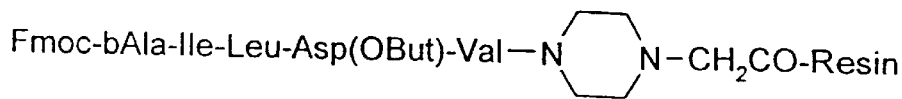
Step 4 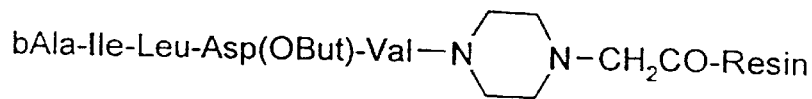
Step 5 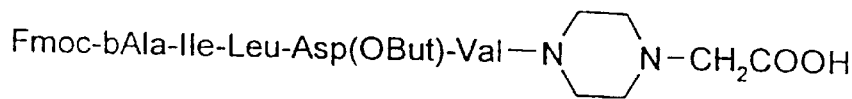
Step 6 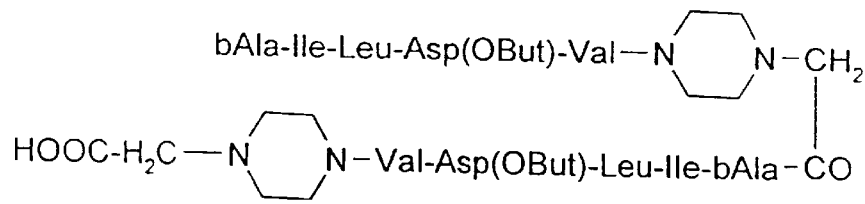
Step 7 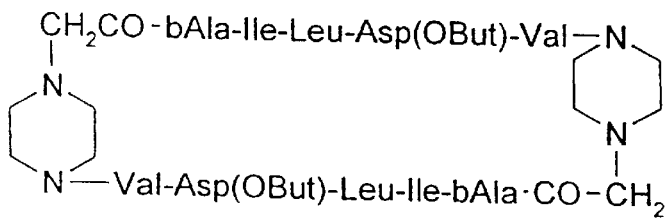
Step 8 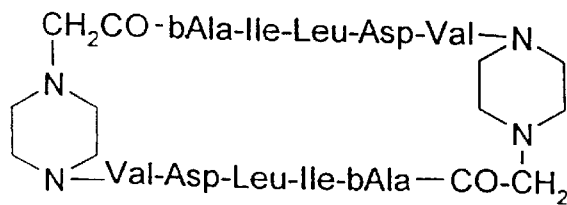

Fig.17.
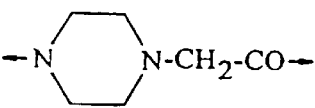   1
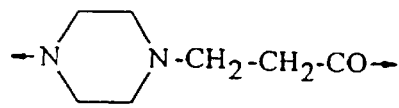   2
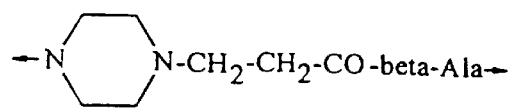   3
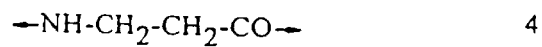   4
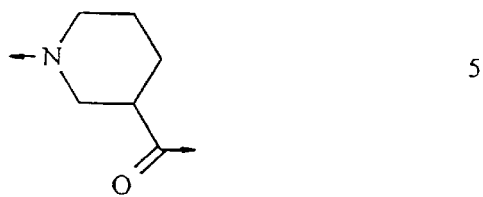   5
   6
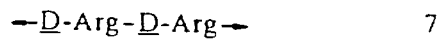   7
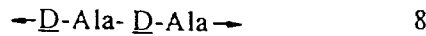   8
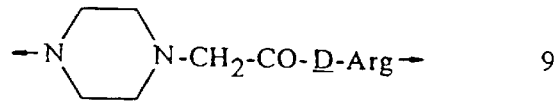   9
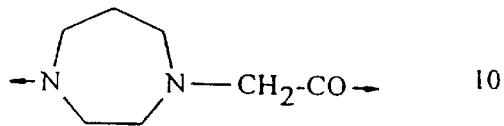   10
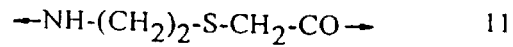   11
   12

PEPTIDE INHIBITORS OF FIBRONECTINE

FIELD OF THE INVENTION

1. Field of the Invention

Many of the cell-cell and cell-extracellular matrix interactions are mediated by protein ligands (e.g. fibronectin, vitronectin and VCAM-1) and their integrin receptors [e.g. VLA-4 (($\alpha 4\beta 1$))]. Recent studies have shown these interactions to play an important role in many physiological (e.g. embryonic development and wound healing) and pathological (e.g. tumour-cell invasion and metastasis, inflammation, atherosclerosis and autoimmune diseases) conditions. Agents which can selectively inhibit some of these interactions are predictably useful for the treatment of a number of diseases.

Integrins are heterodimeric cell surface receptors that are composed of noncovalently associated $\alpha$ and $\beta$ subunits. Using molecular biology and protein chemistry, a number of $\alpha$ and $\beta$ subunits have been identified. The integrin family can be subdivided into classes based on the $\beta$ subunits, which can be associated with one or more $\alpha$ subunits. The most widely distributed integrins belong to the $\beta 1$ class, also known as the very late antigens (VLA). The second class of integrins are leukocyte-specific receptors and consist of one of three $\alpha$ subunits ($\alpha L$, $\alpha M$, or $\alpha X$) complexed with the $\beta 2$ protein. The cytoadhesins $\alpha IIb\beta 3$ and $\alpha v\beta 3$, constitute the third class of integrins.

A wide variety of proteins serve as ligands for integrin receptors. In general, the proteins recognised by integrins fall into one of three classes: extracellular matrix proteins, plasma proteins, and cell surface molecules. Extracellular matrix proteins such as collagen, fibronectin, fibrinogen, laminin, thrombospondin, and vitronectin bind to a number of integrins. Many of these adhesive proteins also circulate in plasma and bind to activated blood cells. Additional components in plasma that are ligands for integrins include fibrinogen and factor X. Cell-bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

2. Description of the Related Art

The target amino acid sequences for many integrins have been identified. For example, the target sequence in $\alpha 5\beta 1$, $\alpha IIb\beta 3$, and $\alpha v\beta 3$, is the Arg-Gly-Asp tripeptide found in proteins such as fibronectin, fibrinogen, thrombospondin, type I collagen, vitronectin and vWF. However, the Arg-Gly-Asp sequence is not the only integrin recognition motif used by adhesive ligands. Another integrin $\alpha 4\beta 1$ binds the variable region (CS1) of fibronectin via the sequence Leu-Asp-Val and the platelet integrin $\alpha IIb\beta 3$ also recognises the sequence His-His-Leu-Gly-Gly-Ala-Lys-Gln-Ala-Gly-Asp-Val at the carboxy-terminus of the gamma chain of fibrinogen.

The present invention principally relates to agents which block the interaction of the ligand VCAM-1 to its integrin receptor VLA-4 ($\alpha 4\beta 1$). [Reference for a review on VLA-4: Structure of the Integrin VLA-4 and Its Cell-Cell and Cell Matrix Adhesion Functions, M. E. Hemler, M. J. Elices, C. Parker and Y. Takada, Immunological Reviews, 114 (1990) 45–65.] Integrin $\alpha 4\beta 1$ is expressed on numerous hematopoietic cells and established cell lines, including hematopoietic precursors, peripheral and cytotoxic T lymphocytes, B lymphocytes, monocytes, thymocytes and eosinophils. Unlike other $\beta 1$ integrins that are involved only in cell-extracellular matrix interactions. $\alpha 4\beta 1$ mediates both cell-cell and cell-extracellular matrix interactions. Cells expressing activated $\alpha 4\beta 1$ bind to the carboxy-terminal cell binding domain of fibronectin (non Arg-Gly-Asp mediated), to VCAM-1 expressed on endothelial cells, and to each other to promote homotypic aggregation. The expression of VCAM-1 by endothelial cells is upregulated by proinflammatory cytokines such as INF-$\gamma$, TNF-$\alpha$ and IL-1$\beta$.

Regulation of $\alpha 4\beta 1$-mediated cell adhesion is important in numerous physiologic processes, including T-cell proliferation. B-cell localisation to germinal centres, and adhesion of activated T cells and eosinophils to endothelial cells. In addition, integrin $\alpha 4\beta 1$-mediated processes are implicated in several diseases such as melanoma cell invasion in metastasis. T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis. Evidence for the involvement of VLA-4/VCAM-1 interaction in the above disease processes has been accumulated by investigating the role of the peptide CS-1 and antibodies specific for VLA-4 or VCAM-1 in various in vitro and in vivo experimental models of inflammation (e.g. contact cutaneous hypersensitivity response in mice), experimental autoimmune encephalomyelitis, lung antigen challenge, diabetes, ulcerative colitis, nephritis and allograft rejection. Further relevant diseases include asthma, psoriasis, restenosis, myocarditis and inflammatory bowel disease.

For example, in an experimental model of arthritis (arthritis induced in inbred female Lewis rats with a single intraperitoneal injection of peptidoglycan-polysaccharide fragments from group A streptococcal cell walls), intravenous administration of CS-1 at the initiation of arthritis (days 0–4; 300 $\mu$g/day) or on days 11 to 16 in animals with established arthritis, was shown to suppress both acute and chronic inflammation. [Reference: Synthetic Fibronectin Peptides Suppress Arthritis in Rats by Interrupting Leukocyte Adhesion and Recruitment, S. M. Wahl, J. B. Allen, K. L. Hines, T. Imamichi, A. M. Wahl, L. T. Furcht and J. B. McCarthy, J. Clin. Invest., 94 (1994) 655–662].

In another model of inflammation (contact hypersensitivity response in oxazalone or 2,4-dinitrofluorobenzene-sensitised mice), intravenous administration of the anti-$\alpha$-4 specific monoclonal antibodies R1-2 or PS/2 (4 to 6 hours prior to challenge) significantly inhibited (50–60% reduction in the ear swelling response) the efferent response. [Reference: Monoclonal Antibodies to the Integrin $\alpha$-4 Subunit Inhibit the Murine Contact Hypersensitivity Response, P. L. Chisholm, C. A. Williams and R. R. Lobb, Eur. J. Immunol., 23 (1993) 682–688]. In an intestinal inflammation model (acute colitis in Cotton-top tamarin), anti-$\alpha$4 integrin monoclonal antibody HP1/2 that binds VLA-4 resulted in significant attenuation of acute colitis. In contrast, two anti-E-selectin monoclonal antibodies (BB11 and EH8) slightly diminished colitis after the 10-day treatment period in Cotton-top tamarin [Reference: Attenuation of Colitis in the Cotton-top Tamarin by Anti-$\alpha$4 Integrin Monoclonal Antibody, D. K. Podolsky, R. Lobb, N. King, C. D. Benjamin, B. Pepinsky, P. Sehgal and M. deBeaumont, J. Clin. Invest., 92 (1993) 372–380].

The antibodies have also been shown to be effective in a model of autoimmune encephalomyelitis (EAE), an inflammatory condition of the central nervous system with similarities to multiple sclerosis. In both diseases, circulating leukocytes penetrate the blood-brain barrier and damage myelin, resulting in impaired nerve conduction and paralysis. EAE can be induced actively by priming an animal to CNS proteins like myelin basic protein (MBP), or adoptively by injection of activated lymphocytes that are specific for these CNS antigens. Various monoclonal antibodies, [MK/1 (anti-VCAM-1) and PS/2 and LPAM-1 (anti α4 integrin)], when injected into irradiated female (PL/J×SJL) F1 mice delayed the onset of disease. When injection of antibody to α4 integrin (LPAM-1 and PS/2) was continued every 3 day until after onset of disease, not only was the onset of disease delayed, but in this case severity of disease was also significantly decreased. [Reference: Surface Expression of α4 Integrin by CD4 T Cells Is Required for Their Entry into Brain Parenchyma, J. L. Baron, J. A. Madri, N. H. Ruddle, J. Hashim and C. A. Janeway, Jr., J. Exp. Med., 177 (1993) 57–68].

Antibodies specific for both α4-integrin (LPAM-1) and one of its ligands, VCAM-1. were also shown to be effective in treating insulin-dependent diabetes mellitus in the non-obese diabetic mouse. Insulin-dependent diabetes mellitus is believed to be an autoimmune disease in which activated T lymphocytes destroy the insulin-producing β-cells of the pancreatic islets. The antibody R1-2 prevented the onset of insulitis in a dose-dependent manner in nonobese diabetic mice. The blocking of disease was accompanied by a marked decrease in lymphocytic infiltration of the islets of Langerhans. [Reference: The Pathogenesis of Adoptive Murine Autoimmune Diabetes Requires an Interaction Between α 4-Integrins and Vascular Cell Adhesion Molecule-1, J. L. Baron, E -P. Reich, I. Visintin and C. A. Janeway, Jr., J. Clin. Invest., 93 (1994) 1700–1708].

Cells expressing integrin α4β1 have been shown to bind to sequences in the heparin II binding domain and the alternatively spliced type III connecting segment (IIICS) located in the carboxy-terminal cell binding domain of fibronectin. Within the IIICS region, α4β1 binds with high affinity to a peptide sequence termed CS-1 (a 25-amino acid peptide), suggesting that this is the major site of α4β1 interaction in fibronectin. The tripeptide Leu-Asp-Val is the minimal sequence within CS-1 capable of supporting hematopoietic cell adhesion or of inhibiting α4β1-mediated cell binding to fibronectin. [References for CS1: The Minimal Essential Sequence for a Major Cell Type-Specific Adhesion Site (CS1) Within the Alternatively Spliced Type III Connecting Segment Domain of Fibronectin is Leucine-Aspartic Acid-Valine, A. Komoriya, L. J. Green, M. Mervic, S. S. Yamada, K. M. Yamada and M. J. Humphries. J. Biol. Chem., 23 (1991) 15075–15079; Activation-Dependent Recognition by Hematopoietic Cells of the LDV Sequence in the V Region of Fibronectin E. A. Wayner and N. L. Kovach. J. Cell Biol., 116 (1992) 489–497.].

In addition to the Leu-Asp-Val containing sequences mentioned above, a cyclic octapeptide 1-adamantaneacetyl-Cys-Gly-Arg-Gly-Asp-Ser-Pro-Cys (containing a disulphide bridge between the two cysteine residues) has been reported to be as effective as the LDV containing peptide Cys-Leu-His-Gly-Pro-Glu-Ile-Leu-Asp-Val-Pro-Ser-Thr in blocking Jurkat cell adhesion to CS-1 coated plates ($IC_{50}$ 30 μM). The cyclic peptide also inhibited the binding of Jurkat cells to fibronectin coated plates. In addition to inhibiting a 4β1-induced adhesion, the octapeptide also inhibited function in αvβ3 as well as αIIbβ IIIa-dependent assays. Therefore the peptide is not selective for α4β1-mediated adhesion. [Reference: Cyclic RGD Peptide Inhibits α4β1 Interaction with Connecting Fragment 1 and Vascular Cell Adhesion Molecule, P. M. Cardarelli, R. R. Cobb, D. M. Nowlin, W. Scholz, F. Gorcsan, M. Moscinski, M. Yasuhara, S -L. Chiang and T. J. Lobl, J. Biol. Chem., 269 (1994) 18668–18673.]

A few small peptides [Reference: Non-peptidic Surrogates of the Leu-Asp-Val Sequence and Their Use in the Treatment of Inflammation. Autoimmune Diseases and Tumour progression, YEDA Research and Development Co. Ltd, WO 94/02445. Publ. date Feb. 3, 1994] have also been reported to inhibit α4β1-induced adhesion.

A disulphide cyclic pentapeptide, Arg-Cys-Asp-thioproline-Cys (thioproline=thiazolidine-4-carboxylic acid), has also been reported to be an inhibitor of leukocyte cell adhesion to fibronectin. In addition, the cyclic peptide also inhibited the binding to the 120 kDa chymotryptic fragment of fibronectin, which contains the Arg-Gly-Asp central cell binding domain. Again, the peptide was not selective. It binds to both α4β1 and α5β1 [Reference: A Novel Cyclic Pentapeptide Inhibits α4β1 and α5β1 Integrin-Mediated Cell Adhesion, D. M. Nowlin, F. Gorcsan, M. Moscinski, S -L. Chiang, T. J. Lobl and P. M. Cardarelli, J. Biol. Chem., 268 (1993) 20352–20359.]

SUMMARY OF THE INVENTION

The present invention is based on the discovery that relatively small dicyclic peptides can potently inhibit the interaction of VCAM-1 with integrin VLA4.

According to one aspect of the present invention there is provided a cyclic dimeric peptide of formula 1 (FIG. 1) wherein:

peptide 1 and peptide 2 independently represent a tetrapeptide of formula -AA1-AA2-AA3-AA4- juxtaposed in parallel or antiparallel orientation;
and
AA1 is an L or D amino acid selected from Ile, Leu and amino analogues thereof selected from Pro, Gly, Tic, Gln and Phe;
AA2 is an L amino acid selected from Leu and amino acid analogues thereof selected from Ile, Phe, Pro and Val;
AA3 is an L amino acid selected from Asp, Glu and amino acid analogues thereof;
AA4 is an L amino acid selected from Val and amino acid analogues thereof selected from Leu, Ile, Phe, Ser, Pro and Cha (cyclohexylalanine);
and
L1 and L2 independently represent linking moieties for linking peptides 1 and 2 to form a cyclic peptide, or salt thereof.

The present invention also provides a cyclic dimeric peptide of formula 1 (FIG. 1) wherein:

peptide 1 and peptide 2 independently represent a tetrapeptide of formula -AA1-AA2-AA3-AA4- juxtaposed in parallel or antiparallel orientation and
AA1 represents an L or D amino acid selected from Ile, Leu, Pro, Gly, Tic, Phe and amino acid analogues thereof
AA2 represents an L amino acid selected from Leu, Ile, Phe, Val and amino acid analogues thereof
AA3 represents an L amino acid selected from Asp, Glu and amino acid analogue thereof
AA4 represents an L amino acid selected from Val, Leu, Ile, Phe, Cha (cyclohexylalanine) and amino acid analogues thereof and
L1 and L2 independently represent linking moieties for linking peptides 1 and 2 to form a cyclic peptide;
or a salt thereof.

In this specification: the tetrapeptide -AA1-AA2-AA3-AA4- has its N-terminus at AA1 and its C-terminus at AA4 unless otherwise stated; and amino acids have L configuration unless otherwise stated.

The cyclic peptide preferably has an $IC_{50}$ of <20 μM, more preferably <15 μM, in the MOLT-4 cell/fibronectin assay described herein or the peptide having an $IC_{50}$ of <100 μM, preferably <50 μM, in the MOLT-4 cell/recombinant soluble VCAM-1 assay described herein. Preferably AA1–4 have the general formula 4 (FIG. 4) wherein R is the amino acid side chain and $R^2$ and $R^3$ independently represent H or C1 alkyl (preferably H or Me, especially H).

When peptides 1 & 2 are in antiparallel juxtaposition L1 and L2 preferably have the general Formula 5 (FIG. 4) in which $R^4$ represents H or $C_{1-4}$alkyl (especially H), and X is selected from —$(CH_2)_n$ wherein n=1–4 optionally substituted on $CH_2$ with $C_{1-4}$alkyl; and —$(CH_2)$, wherein n=1–4 optionally substituted on —$CH_2$ with $NH_2$; or X and $NR^4$ together represent a group of Formula 8. Formula 8a or Formula 9 (FIG. 4) in which n=0–4.

When peptides 1 & 2 are in parallel juxtaposition L1 and L2 preferably have the general Formulas 7 and 6 (FIG. 4) respectively in which $R^5$ and $R^6$ independently represent H or $C_{1-4}$alkyl (especially H), X represents —$(CH_2)_n$ wherein n=1–4 optionally substituted on CH, with $C_{1-4}$alkyl or:

X and $NR^5$ together represent a group of Formula 8, Formula 8a or Formula 9 (FIG. 4) in which n=0–4 or;

X and $NR^6$ together represent a group of Formula 8, Formula 8a or Formula 9 (FIG. 4) in which n=0–4;

provided that if both X & $NR^5$ and X & $NR^6$ represent any combination of formulas 8, 8a or 9 then the —$(CH_2)_n$ motif is not duplicated.

Preferred values are:
AA1 is Ile
AA2 is Leu
AA3 is Asp
AA4 is Val

Preferred Ile analogues are shown in FIG. 8.
Preferably peptides 1 & 2 are in antiparallel juxtaposition. Preferably L1 and L2 are identical.

Suitable values for AA1 include tert-Leu and tert-butyl-Ala. Further suitable values for AA1 include D-Leu. MeIle and MePhe. A further suitable value for AA2 is Nle, and for AA4 Leu, Nva or Nle.

Preferred values for L1 and L2 are shown in FIG. 7 for when peptides 1 & 2 are in antiparallel juxtaposition. Preferred values for L1 and L2 are shown in FIG. 12 for when peptides 1 & 2 are in parallel juxtaposition. Further preferred values for L1 and L2 are shown in FIG. 17.

The cyclic dipeptides of the present invention have at least one of the following advantages: they are more potent than known compounds, e.g. CS1 and the compound claimed in the YEDA patent in our tests; they are smaller than CS-1, a 25-amino acid peptide, and therefore easier to synthesise and; cyclic peptides are more stable to enzymic degradation.

The compound number 1 (Table 2) is an especially preferred compound as are compound numbers 11 to 14. Especially preferred compounds have shown activity in in vivo screens [in the mouse in vivo CHS (contact hypersensitivity) model]—See Example 2 below. CSI at 10 mg/kg/day and 1 mg/kg/day gave 0% inhibition. No toxicity was observed for compounds tested of the present invention at the effective dose.

According to a further feature of the invention there is provided a pharmaceutical composition which comprises a cyclic dipeptide of the invention in association with a pharmaceutically acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. The composition may be in a form suitable for topical administration such as for example creams, ointments and gels. Skin patches are also contemplated. Formulation in general is described in Chapter 25.2 of Comprehensive Medicinal Chemistry, Volume 5, Editor Hansch et al, Pergamon Press 1990.

In general the above compositions may be prepared in a conventional manner using conventional excipients. However, in the case of a composition for oral administration, it may be convenient for the composition to include a coating to protect the cyclic dipeptide active ingredient from the actions of enzymes in the stomach.

A preferred composition of the invention is one suitable for oral administration in unit dosage form for example a tablet or capsule which contains from 2.5 to 500 mg, and preferably 10 to 100 mg, of cyclic dipeptide in each unit dose, or one suitable for parenteral administration which contains from 0.5 to 100 mg of cyclic dipeptide per ml. and preferably 1 to 10 mg of cyclic dipeptide per ml of solution.

A parenteral composition is preferably a solution in isotonic saline or isotonic dextrose buffered if necessary to a pH of 5 to 9. Alternatively, the parenteral composition may be one designed for slow release over a period of at least 5 days, in which case the amount of polypeptide per unit dose is in general greater than that required when a conventional injectable formulation is used. A preferred slow release formulation is a continuous release formulation, for example a formulation of the type described in European Patent Specification No. 58481. A preferred slow release parenteral formulation contains from 10 to 100 mg of cyclic dipeptide per unit dose.

The composition of the invention will normally be administered such that a daily oral dose will be from 0.1 mg/kg, to 50 mg/kg and a daily parenteral dose, will be from 20 micrograms/kg to 10 mg/kg.

Accordingly, the invention provides a cyclic dipeptide as herein described for use as a medicament.

According to a further feature of the invention there is provided a method for inhibiting the interaction between VCAM-1 and/or fibronectin and the integrin receptor VLA-4 in warm-blooded animals i.e. mammals such as man in need of such treatment which comprises administering to said mammal an effective amount of 4 cyclic dipeptide of formula 1 or a pharmaceutically acceptable salt thereof. In a preferred embodiment the mammal in need of treatment is suffering from multiple sclerosis, asthma or rheumatoid arthritis. The invention also provides the use of such a cyclic dipeptide of formula 1 or a pharmaceutically-acceptable salt thereof in the production of a new medicament for use in the treatment of a disease or medical condition mediated by the interaction between VCAM-1 and the integrin receptor VLA-4

Synthetic Details

A cyclic dimeric peptide of the invention of formula 1 may be prepared by any process well known in the art of peptide chemistry to be applicable to the synthesis of analogous compounds. Thus, for example, a cyclic dipeptide of the invention may be obtained by procedures analogous to those disclosed in "Solid Phase Peptide Synthesis: A practical approach" by Atherton and Sheppard (published by IRL press at Oxford University Press, 1989), "Solid Phase Peptide Synthesis" by Stewart and Young (published by the Pierce Chemical Company, Illinois, 1984), "Principles of Peptide Synthesis" (published by Springer-Verlag, Berlin, 1984) "Practice of Peptide Synthesis" (published by Springer-Verlag, Berlin, 1984), and a series of books "Amino Acids, Peptides and Proteins" (volumes 1–25; volume 25 published in 1994) (published by the Royal Society of Chemistry, Cambridge, U.K.). Synthesis may be achieved by automated or manual means.

Preferred processes for the manufacture of a cyclic dipeptide of the invention include:

(a) The removal of one or more conventional peptide protecting groups from a protected cyclic dipeptide of Formula 10 (FIG. 10) wherein Pr1 represents a protecting group on the acid group in the side chain of AA3 to give a cyclic dipeptide of the invention of formula 1 and optionally, simultaneously or subsequently, also removing any additional conventional peptide protecting groups;

(b) The formation of an amide bond by coupling two peptide units, one containing a carboxylic acid group, or a reactive derivative thereof, and the other containing an amino group, such that a protected or unprotected cyclic dimeric peptide having the sequence indicated in formula 1 is produced, if necessary, the protecting groups are removed using process (a) above.

BRIEF DESCRIPTION OF THE DRAWINGS

The invention will now be illustrated by the following non-limiting examples in which

FIG. 4 illustrates Formulas 4–9

FIG. 5 illustrates synthesis of compound 5 (Table 2)

FIG. 6 illustrates synthesis of compound 8 (Table 2).

FIG. 7 illustrates preferred linkers for antiparallel juxtapositions of peptides 1 & 2

FIG. 8 illustrates analogues of Ile.

FIG. 9 illustrates Tic (1) and nipecotic acid (2)

FIG. 10 illustrates Formula 10

FIG. 11 illustrates a detailed structure of compound 1 (Table 2)

FIG. 12 illustrates preferred linkers for parallel juxtapositions of peptides 1 & 2

FIG. 14 illustrates synthesis of compound 1 (Table 2), second route

FIG. 15 illustrates synthesis of compound 3 (Table 2)

FIG. 16 illustrates synthesis of compound 4 (Table 2)

FIG. 17 illustrates preferred linkers

In the Figures arrowed bonds indicate attachment points only (ie not a —CH$_2$ group). Illustrations of attachment points will be such that a nitrogen atom will link to a —C(O)— and vice versa unless otherwise stated or implicit.

Table 1 illustrates synthesis and purification of cyclic dipeptides.

Table 2 illustrates characterisation of cyclic dipeptides.

Abbreviations:

| | |
|---|---|
| Boc | tert-butoxycarbonyl |
| Cha | cyclohexylalanine |
| Dab | 2,4-diamino-butyric acid |
| Fmoc | 9-fluorenylmethoxycarbonyl |
| Nle | norleucine |
| Orn | ornithine |
| Pbf | 2,2,4,6,7-Pentamethyldihydrobenzenefuran-5-sulphonyl |
| Tic | 1,2,3,4-tetrahydroisoquinoline-3-carboxylic acid |
| Z | benzyloxycarbonyl |

All temperatures are in degrees centigrade unless otherwise stated.

DESCRIPTION OF PREFERRED EMBODIMENTS

EXAMPLE 1

Synthesis of Compounds 1–16 (Table 2)

1. Synthesis of Compound 1

Figure 1:
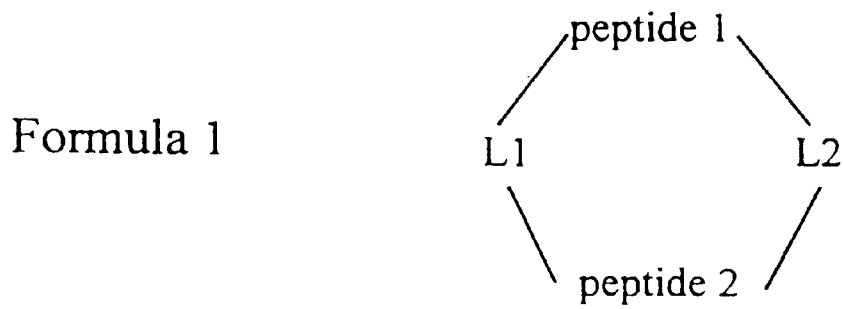
FIG. 1 illustrates Formula 1
Figure 2:
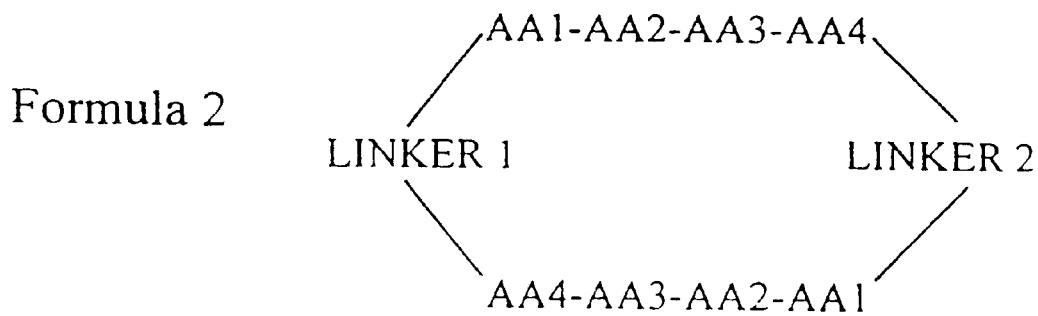
FIG. 2 illustrates peptides 1 & 2 in antiparallel juxtaposition.
Figure 3:
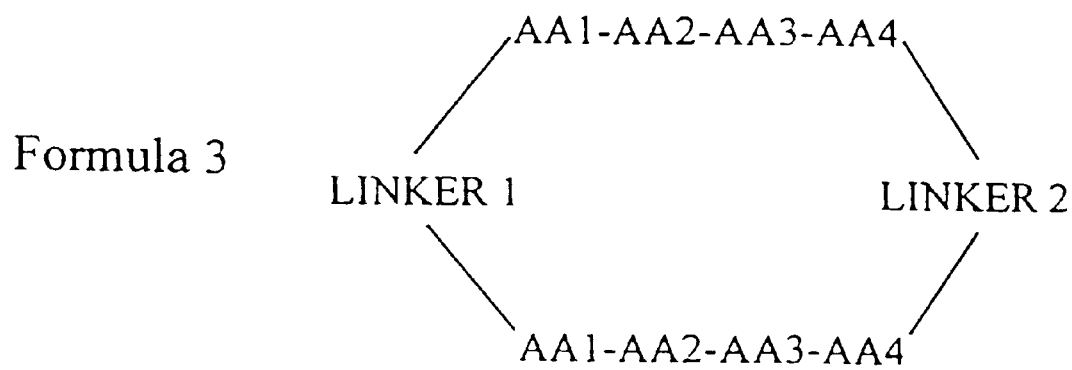
FIG. 3 illustrates peptides 1 & 2 in parallel juxtaposition.
Figure 13:
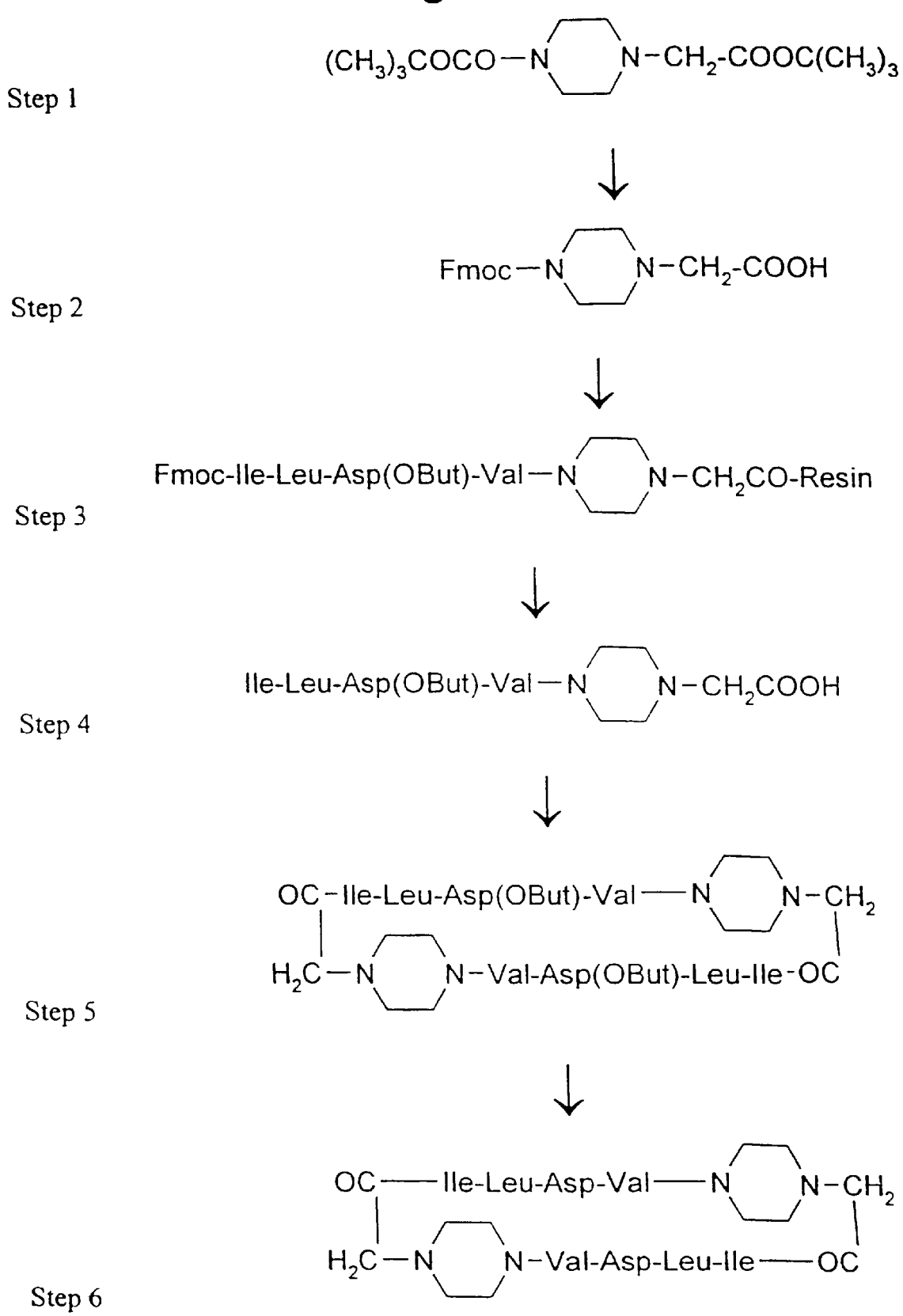
FIG. 13 illustrates synthesis of compound 1 (Table 2)

(Figure 13)

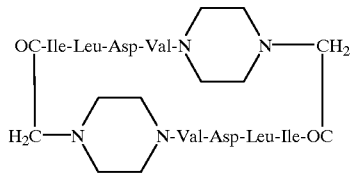

The cyclic dipeptide was prepared by two different routes. In each of these methods, the required linear peptide was prepared by solid phase peptide synthesis techniques using 2-chlorotritylchloride resin. The synthetic schemes are shown in FIGS. 13 and 14 and the details are described below in this section and in section 2. After assembling the protected peptide on the resin, the linear peptide was cleaved from the resin and used in the subsequent steps without any purification. However, the final product was purified extensively by reverse phase high pressure liquid chromatography (HPLC) before characterisation.

1.1. Synthesis of (Figure 13, Step 1)

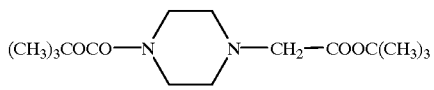

t-Butyl bromoacetate (4.88 g, 25 mmoles) in dichloromethane (50 ml) was added to a solution of t-butyl-1-piperazine carboxylate (4.65 g, 25 mmoles) and triethylamine (3.5 ml, 25 mmoles) in dichloromethane (30 ml). The reaction mixture was stirred overnight, filtered to remove the solids separated overnight and the filtrate evaporated to dryness. The residue was partitioned between ethyl acetate and water, the organic layer was then washed with water, dried over MgSO$_4$ and evaporated to dryness. The residue was crystallised from ether-isohexane to yield the product (5.66 g, 75%, m.p. 99–100° C.). [Elemental analysis: Found C, 59.8%; H, 9,6%; N, 9.1%; C$_5$H$_{28}$N$_2$O$_4$ requires C, 60.0%; H, 9.4%; N, 9.33%]. [Thin layer chromatography on silica gel plates showed a single spot; R$_f$ 0.38 in ethyl acetate-isohexane (1:1) and 0.68 in methanol-chloroform (1:9)].

1.2. Synthesis of

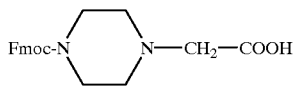

(Figure 13, Step 2)

The compound described in section 1.1 (5 g, 16.6 mmoles) was treated with a mixture of trifluoroacetic acid-water (95:5. 50 ml) for 1 hour. The acid was removed by evaporation in vacuo and the residual oil was triturated with ether to give a solid which was collected, washed with ether and dried over $P_2O_5$/KOH under vacuum (6.25 g, m.p. 177–182° C.). The solid was then dissolved in a mixture of water and acetone (1:1, 150 ml) containing potassium carbonate (6.92 g, 3 equivalents). 9-Fluorenylmethyl-N-hydroxysuccinimide (5.66 g, 16.7 mmoles) in acetone (30 ml) was added over a period of minutes with stirring. The pH of the solution was maintained at about 9 by the addition of M $K_2CO_3$ solution. After stirring overnight at room temperature, the acetone was removed by evaporation under vacuum and the aqueous solution was acidified with $KHSO_4$ solution. The product was extracted into ethyl acetate and the solution was washed with water (6 times) and with saturated NaCl solution. The organic layer was dried over $MgSO_4$ and evaporated to give an oil which solidified on trituration with isohexane and ether (yield 3.72 g, 60%). A sample was recrystallised from ethanol-ether. m.p. 179–182° C., $MH^+367$.

1.3. Synthesis of

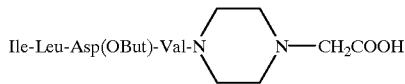

(Figure 13, Step 3 and 4)

The Fmoc-piperazine derivative (366 mg, 1 mmole) in dichloromethane (15 ml) and diisopropylethylamine (525 μl, 3 equivalents) was added to 2-Chlorotritylchioride resin (Nova Biochem. 1 g) and the reaction mixture was shaken gently for 75 minutes. A 10% solution of diisopropylethylamine in methanol (10 ml) was added and the shaking was continued for 10 minutes. The resin was filtered off, washed successively with methylene chloride, dimethylformamide, methylene chloride, ether and dried at 50° C. in a vacuum oven (weight 1.13 g).

The above resin was placed in a reaction vessel fitted with a sintered glass disc. The following series of reactions were then carried out manually to obtain the desired to peptide resin.
(a) Removal of the Fmoc group with two treatments (1×5 minutes and 1×15 minutes) of 20% piperidine in dimethylformamide.
(b) Dimethylformamide washes (5).
(c) Acylation with Fmoc-Val (678 mg, 2 mmole) activated with O-(benzotriazol-1-yl)-1,1,3,3-tetramethyluronium hexafluorophosphate (HBTU) (760 mg, 2 mmole) and diisopropylethylamine (700 μl, 4 mmole) in dimethylformamide (4 ml) for 1 hour.
(d) Dimethylformamide washes (5)

The above deprotection and coupling cycles were repeated using Fmoc-Asp(OBu$^t$) (822 mg, 2 mmoles), Fmoc-Leu (700 mg, 2 mmoles) and Fmoc-Ile (700 mg, 2 mmoles) to give the protected tetrapeptide derivative attached to the chlorotrityl resin. The N-terminal Fmoc group was cleaved with 20% piperidine in dimethylformamide (1×5 minutes and 1×15 minutes) and the peptide resin was washed successively with dimethylformamide, methylene chloride and ether and dried in a vacuum oven at 50° C.

The peptide resin was suspended in a mixture of acetic acid-trifluoroethanol-methylene chloride (2:2:6) (25 ml) for 2 hours. The resin was removed by filtration, washed with the above solvent mixture. The combined filtrates were evaporated and the residue triturated with ether to give the linear tetrapeptide derivative as an acetate salt. The acetate salt was then converted to a hydrochloride salt by dissolving it in a mixture of water-acetonitrile (2:1, 60 ml), cooling to 0° C., adding 1.05 equivalents of 1N HCl and freeze drying the contents.

1.4. Synthesis of

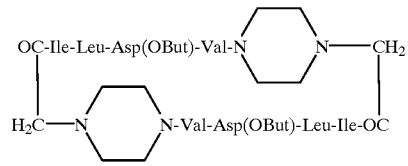

(Figure 13, Step 5)

The linear peptide hydrochloride (388 mg, 0.57 mmole) was dissolved in dimethylformamide (600 ml) and O-(benzotriazol-1-yl)-1,1,3,3-tetramethyluronium hexafluorophosphate (HBTU) (218 mg, 0.57 mmoles), was added followed by diisopropylethylamine (300 μl, 1.72 mmoles). The reaction mixture was stirred for 24 hours at room temperature and then evaporated to dryness under vacuum.

1.5. Synthesis of

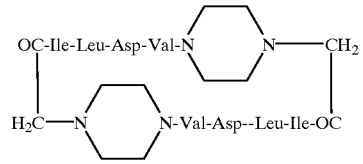

(Figure 13, Step 6)

The crude cyclic dipeptide was treated for 1 hour with a mixture of trifluoroacetic acid-water (95:5, 25 ml) and triisopropylsilane (200 μl) to remove the aspartic acid side chain protecting groups. Evaporation to a small volume, followed by trituration with ether yielded the crude cyclic peptide which was purified by preparative reverse phase HPLC on a Vydac 218TP1022 column using a gradient of acetonitrile-water containing 0.1% trifluoroacetic acid (20–50%) over a period of 65 minutes at a flow rate of 10.0 ml/minute. The product-containing fractions were combined and freeze dried to give the purified cyclic peptide (46 mg). The peptide was characterised by amino acid analysis and mass spectroscopy.

2. Synthesis of Compound 1 (Second route, FIG. 14).

The second route shown in FIG. 14 involved the synthesis of a linear octapeptide derivative (structure shown below) in place of the tetrapeptide derivative used in the first route. The first three steps in both routes 1 and 2 are the same.

2.1. Synthesis of Compound 1 (Steps 4 and 5, FIG. 14).

The Fmoc protected tetrapeptide resin obtained in step 3 (FIG. 14) was divided in two parts. One half of the resin was treated in the standard manner with piperidine to cleave the N-terminal Fmoc group to give the partially protected tetrapeptide derivative still attached to the resin (step 4). The other half was treated in a standard fashion with a mixture of acetic acid-trifluoroethanol-methylene chloride (2:2:6) to cleave the Fmoc Protected tetrapeptide derivative from the resin (step 5).

The Fmoc protected fragment (800 mg, 0.93 mmole) was then coupled to the tetrapeptide fragment still attached to the resin by the standard method (HBTU, 352 mg, 0.93 mmole, diisopropylethylamine 325 μl, 1.85 mmole) used to couple various amino acid derivatives during the chain elongation process.

2.2. Synthesis of Compound 1 (Steps 6, 7 and 8, FIG. 14).

The linear octapeptide derivative assembled on the resin was deblocked at the N-terminal end (Fmoc cleavage), cleaved from the resin, cyclised and deprotected [Asp(OBut) cleavage] by the standard methods used in the first route. The dimeric peptide was then purified by using the solvent system described in table 1 (yield 374 mg).

3. Synthesis of Compound 2

The peptide was prepared by the first route described above for the corresponding Ile containing compound 1. HPLC analysis indicated the product to be a mixture of the required dimer (38%) and a cyclic monomer (62%). Reverse phase HPLC purification using the solvent system described in table 1 gave the desired dimeric peptide which was characterised by amino acid analysis and mass spectroscopy (table 2).

4. Synthesis of Compound 3 (FIG. 15)

The linear peptide required for the synthesis of this cyclic dipeptide (table 1) was assembled on the 2-chlorotritylchloride resin. 3-Bromopropionic acid was reacted with the resin in a manner similar to that described above for the Fmoc-piperazine derivative in example 1.3 (compound 1). A five-fold excess of piperazine was then added to the 3-bromopropionyl-O-(2-chlorotrityl)-resin to give piperazine-N-propionyl derivative linked to the resin (structure shown below in step 1, FIG. 15)

Fmoc-Val, Fmoc-Asp(OBut), Fmoc-Leu and Fmoc-Ile were then coupled to the resin by the procedures described in section 1.3 to give the Fmoc-tetrapeptide piperazinyl derivative. Piperidine treatment in a standard manner to cleave the N-terminal Fmoc group gave the partially protected tetrapeptide derivative shown in step 2 (FIG. 15). Further coupling and deprotection reactions using 3-bromopropionic acid, piperazine, Fmoc-Val, Fmoc-Asp (OBut), Fmoc-Leu and Fmoc-Ile by the standard procedures gave the octapeptide derivative containing two piperazine groups (step 4, FIG. 15). The peptide was then cleaved from the resin, cyclised, deprotected and purified by the procedures described above for compound 1.

5. Synthesis of Compounds 4 and 5

Both these compounds were synthesised by the second route described above for the synthesis of compound 1 (FIG. 14). As shown in FIGS. 16 and 5, one of the fragments with a free amino group at the N-terminus was left attached to the resin and a second fragment containing an Fmoc group at the N-terminus was cleaved from the resin. The second fragment containing a C-terminal carboxyl group was activated by the HBTU method and coupled to the fragment still attached to the resin.

The linear peptide derivatives assembled on the resin were deblocked at the N-terminal end (Fmoc cleavage), cleaved from the resin cyclised and deprotected [Asp(OBut) cleavage] by the standard methods used in the synthesis of compound 1. The dimeric peptides were then purified by using the solvent systems described in table 1.

6. Synthesis of Compound 6

Starting from β-alanine, the linear decapeptide, D-Leu-Leu-Asp(OBut)-Val-β-Ala-D-Leu-Leu-Asp(OBut)-Val-β-Ala, was assembled on the chlorotritylresin. The rest of the synthesis (cleavage, cyclisation and deprotection) was similar to that of compound 1.

7. Synthesis of Compound 7

7.1. The peptide was prepared by the dimerisation of the linear peptide (structure shown below) which was assembled on the 2-chlorotritylchloride resin by the method described below.

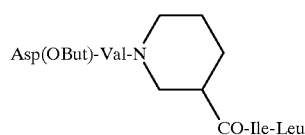

A solution of Fmoc-Leu (700 mg, 2 mmole) and disopropylethylamine (1.05 ml, 6 mmole) in dry dichloromethane (20 ml) was added to a suspension of 2-chlorotritylchloride resin (2 g) in dichloromethane (10 ml), and the reaction mixture was shaken gently for 75 minutes. A 10% solution of diisopropylethylamine in methanol (10 ml) was added and shaking was continued for a further 10 minute period. The resin was filtered off, washed successively with dichloromethane, dimethylformamide, dichloromethane and ether and dried at 50° C. in a vacuum oven (weight 2.4 g).

The above resin was placed in a reaction vessel fitted with a sintered glass disc. The following series of reactions were then carried out manually to obtain the desired peptide resin.

(a) Removal of the Fmoc protecting group with two treatments (1×5 min., 1×15 min.) of 20% piperidine in dimethylformamide followed by five washes with dimethylformamide.

(b) Acylation of the Leu resin with Fmoc-Ile (1.42 g, 4 mmole) activated with O-(benzotriazol-1-yl),1,1,3,3,-tetramethyluronium hexafluorophosphate (HBTU) (1.52 g, 4 mmole) and diisopropylethylamine (1.4 ml, 8 mmole) in dimethylformamide (8 ml) for 30 minutes. After the reaction, the resin was washed five times (as above) with dimethylformamide to remove the excess reagents and dried. Only half of the Fmoc-Ile-Leu resin thus obtained was used in the next step.

(c) The above deprotection and coupling cycles (a and b) were repeated using Fmoc-nipecotic acid (702 mg, 2 mmole), Fmoc-Val (678 mg 2, mmole) and Fmoc-Asp (OBut) (822 mg, 2 mmole) to give the required partially protected tetrapeptide attached to the resin. The peptide was cleaved from the resin by two treatments with acetic acid-trifluoroethanol-dichloromethane (2:2:6; 15 ml ) for 1 hour. The resin was removed by filtration and washed with the above deblocking solvent mixture. The combined filtrates were evaporated and the residue triturated with ether to give the linear partially protected tetrapeptide as an acetate salt. The peptide was converted to a hydrochloride salt by dissolving in water-acetonitrile (2:1:60 ml), cooling to 0° C. adding 1.05 equivalents of 1N HCl and freeze drying.

7.2. Synthesis of Compound 7

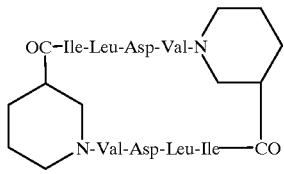

The linear peptide hydrochloride (350 mg, 0.51 mmole) was dissolved in dimethylformamide (500 ml) and HBTU (194 mg, 0.51 mmole) was added followed by diisopropylethylamine (268 μl, 1.53 mmole). The reaction was monitored by reverse phase HPLC. After 3 hours, when no starting material could be detected, the reaction mixture was evaporated to dryness and the residue treated with a mixture of trifluoroacetic acid-water (95:5; 25 ml) and triisopropylsilane (500 μl) for one hour. After evaporation to low volume ether was added and the crude product collected by filtration. HPLC analysis indicated the product to be a mixture of the required dimer (72%) and a cyclic monomer (28%). Reverse phase HPLC purification using the solvent system described in table 1 gave the desired dimeric peptide which was characterised by amino acid analysis and mass spectroscopy (table 2).

8. Synthesis of Compound 8, c(D-Arg-MeIle-Leu-Asp-Val-D-Arg-MeIle-Leu-Asp-Val), (FIG. 6)

The cyclic peptide was prepared by the solid phase procedure using 2-chlorotritylchloride resin. The synthetic details are described below. After assembling the partially protected linear peptide on the resin, the peptide was cleaved from the resin and used in the subsequent steps without any purification. However, the final product was purified extensively by reverse phase high pressure liquid chromatography (HPLC) before characterisation.

8.1. Preparation of Fmoc-Val-chlorotrityl resin (step 1, FIG. 6)

2-Chlorotritylchloride resin (Alexix Corporation: 1.35 mmole Cl/g; 5 g) was swollen in dichloromethane (30 ml) (dried over molecular sieve) for 5 minutes. A solution of Fmoc-Val (1.7 g, 5 mmole) and diisopropylethylamine (2.63 ml. 15 mmole) in dichloromethane (25 ml) was added and the suspension was shaken mechanically for 45 minutes. Methanol (9 ml) and diisopropylethylamine (1 ml) were added and the shaking was continued for a further five minute period. The resin was collected by filtration and washed successively with dichloromethane, dimethylformamide, dichloromethane. isopropanol and ether, and finally dried at 50° C. in a vacuum oven (weight 5.25 g)

8.2. Preparation of D-Arg(Pbf)-MeIle-Leu-Asp(OBu')-Val-D-Arg(Pbf)-MeIle-Leu-Asp(OBut)-Val-chlorotrityl resin (steps 2 and 3. FIG. 6)

The above Fmoc-Val resin (2 g) was placed in a reaction vessel fitted with a sintered glass disc. The following series of reactions were then carried out manually to obtain the desired peptide resin.

(a) Removal of the Fmoc group with two treatments (1×5 minutes and 1×15 minutes) of 20% piperidine in dimethylformamide followed by five washes with dimethylformamide to remove excess reagents and cleavage products.

(b) Acylation with Fmoc-Asp(OBut) (2.06 g, 5 mmole), activated with O-(benzotriazol-1-yl)-1,1,3,3-tetramethyluronium hexafluorophosphate (HBTU) (1.90 g, 5 mmole) and diisopropylethylamine (1.75 ml. 10 mmole) in dimethylformamide (8 ml) for 1 hour. The resin was again washed five times with dimethylformamide to remove excess reagents.

The above deprotection and coupling cycles were repeated using Fmoc-Leu (1.78 g, 5 mmole), Fmoc-MeIle (1.84 g. 5 mmole), Fmoc-D-Arg(Pbf) (3.76 g, 5 mmole) to give Fmoc-D-Arg(Pbf)-MeIle-Leu-Asp(OBut)-Val-chlorotritylresin. Further elongation of this pentapeptide resin to give the protected decapeptide resin was carried out using one half of the resin. The deblocking and coupling reactions on this pentapeptide resin were continued using Fmoc-Val (850 mg, 2.5 mmole), Fmoc-Asp(OBut) (1.03 g, 2.5 mmole), Fmoc-Leu (855 mg, 2.5 mmole) Fmoc-MeIle (920 mg, 2.5 mmole), Fmoc-D-Arg(Pbf) (1.87 g, 2.5 mmole), As in the case of compound 1. coupling of the Fmoc-D-Arg derivative was achieved by using O-(7-azabenzotriazol-1-yl)-1,1,3,3-tetramethyluronium hexafluorophosphate (HATU) and diisopropylethylamine. The N-terminal Fmoc group was cleaved (step 3) with 20% piperidine in dimethylformamide (1×5 minutes and 1×15 minutes) and the peptide resin, D-Arg(Pbf)-MeIle-Leu-Asp (OBu')-Val-D-Arg(Pbf)-MeIle-Leu-Asp(OBut)-Val-chlorotrityl resin, was washed successively with dimethylformamide, dichloromethane and ether and dried in a vacuum oven at 50° C.

8.3. Preparation of D-Arg(Pbf)-MeIle-Leu-Asp(OBu')-Val-D-Arg(Pbf)-MeIle-Leu-Asp(OBu')-Val, HCl. (step 4, FIG. 6)

The peptide resin, D-Arg(Pbf)-MeIle-Leu-Asp(OBu')-Val-D-Arg(Pbf)-MeIle-Leu-Asp(OBu')-Val-chlorotrityl resin, was suspended in a mixture of acetic acid-trifluoroethanol-dichloromethane (2:2:6) (25 ml) for 1 hour. The resin was removed by filtration and retreated with the same mixture for a further one hour. The combined filtrates were evaporated and the residue triturated with ether to give D-Arg(Pbf)-MeIle-Leu-Asp(OBu')-Val-D-Ard(Pbf)-MeIle-Leu-Asp(OBu')-Val as an acetate salt (1.34 g). The acetate salt was then converted to a hydrochloride salt by dissolving it in a mixture of water-acetonitrile (2:1, 60 ml), cooling to 0° C., adding 1.05 equivalents of 1N HCl and freeze drying the contents.

8.4. Preparation of c(D-Arg(Pbf)-MeIle-Leu-Asp(OBu')-Val-D-Arg(Pbf)-MeIle-Leu-Asp(OBu')-Val) (step 5, FIG. 6)

The above linear peptide hydrochloride, D-Arg(Pbf)-MeIle-Leu-Asp(OBu')-Val-D-Arg(Pbf)-MeIle-Leu-Asp (OBu')-Val (HCl), (1.34 g, 0.7 mmole) was dissolved in dimethylformamide (700 ml) and O-(7-aza-benzotriazol-1-yl)-1,1,3,3-tetramethyluronium hexafluorophosphate (HATU) (264 mg, 0.7 mmole), and dissopropylethylamine (370 μl, 2.1 mmole) were added to the solution. The cyclisation reaction was monitored by analytical HPLC. On completion of the reaction (2 hours at room temperature), the reaction mixture was evaporated to dryness in vacuum, ether was added and the solid collected by filtration. The product [retention time 22.06 minutes on a Vydac 218TP54 column using a gradient of acetonitrile-water containing 0.1% trifluoroacetic acid (60–95%) over a period of 30 minutes at a flow rate of 1.0 ml/minute] was used in the next step without any purification.

8.5. Preparation of c(D-Arg-MeIle-Leu-Asp-Val-D-Arg-MeIle-Leu-Asp-Val) [compound 8](step 6, FIG. 6)

The above protected cyclic peptide, c(D-Arg(Pbf)-MeIle-Leu-Asp(OBu')-Val-D-Arg(Pbf)-MeIle-Leu-Asp(OBu')-Val) was treated for 150 minutes with a mixture of trifluoroacetic acid-water (95:5, 30 ml) and triisopropylsilane (1 ml) to remove the arginine and aspartic acid side chain protecting groups. Evaporation to a small volume, followed by trituration with ether yielded the crude cyclic peptide (1.06 g). The crude product was purified by preparative reverse phase HPLC on a Deltapak $C_{18}$ column (30×30 mm) using a gradient of acetonitrile-water containing 0.1% trifluoro acetic acid (20–36%) over a period of 80 minutes at a flow rate of 30.0 ml/minute. The product-containing fractions were combined and freeze dried to give the purified cyclic peptide (280 mg). The peptide [single peak on HPLC. retention time 29.60 minutes on a Vydac 218TP54 column using a gradient of acetonitrile-water containing 0.1% trifluoroacetic acid (20–45%) over a period of 30 minutes at a flow rate of 1.0 ml/minute] was characterised by amino acid analysis and mass spectroscopy (table 2).

9. Syntheses of Compounds 9 and 10

Both these compounds were synthesised by the same procedure as described above for compound 8.

10. Syntheses of Compounds 11 to 14

The peptides were synthesised by the second route used for compound 1 (section 2. FIG. 14). The linear octapeptide derivatives for compounds 11. 12 and 14 and a decapeptide derivative for compound 13 (sequences shown in table 1) were first assembled on the resin followed by cleavage, cyclisation and deprotection by the methods described above to give the required products.

11. Synthesis of Compound 15

Compound 15 was synthesised by the same procedure as described above for compound 8 except that the unusual linking group —NH(CH$_2$)$_2$—S—CH$_2$—CO— was incorporated by using Fmoc—NH(CH$_2$)$_2$—S—CH$_2$—COOH. Synthesis of this derivative is described below.

Fmoc—NH(CH$_2$)$_2$—S—CH$_2$—COOH (used above) was obtained from 2-aminoethanethiol and 2-bromoacetic acid, 2-Aminoethanethiol hydrochloride (5.68 g, 50 mmole) was dissolved in water (200 ml) and sodium hydrogen carbonate (25.2 g, 300 mmole) was added to it. 2-Bromoacetic acid (6.95 g, 50 mmole) dissolved in acetonitrile (100 ml) was added in portions over 30 minutes to the stirred solution prepared above. After 1 hour at room temperature, a solution of 9-fluorenylmethyl-N-hydroxysuccinimide (Fmoc-OSu) (16.85 g. 50 mmole) in acetonitrile (150 ml) was added and the stirring was continued for 16 hours. The slightly turbid solution was evaporated to remove most of the acetonitrile and the remaining aqueous solution was extracted with ethyl acetate (3×50 ml) and acidified (pH 2) by the addition of hydrochloric acid. The white solid was collected, washed with water and dried in vacuo at 45° C. Yield 17 g (95%), (M+H)$^+$358.0.

12. Synthesis of Compound 16

Compound 16 was synthesised by the same procedure as described above for compound 8.

EXAMPLE 2

In Vitro and In Vivo Assays

The following abbreviations and sources of materials are used in the following examples.

MOLT-4 cells—lymphocytic T cell line (ATCC derived)

Fibronectin—Reagent grade human fibronectin. Purified from human plasma by gelatin-sepharose affinity chromatography. Source: Bio Products Elstree UK. Product No. 9136. A review article on fibronectins is Fibronectins—Adhesive Glycoproteins of Cell Surface and Blood, K. M. Yamada and K. Olden, Nature, 275 (1978) 179–184.

rsVCAM-1—(Reference source: Biochem Biophys Res Comm 1991 178 N3; 1498–1504).

VCAM-1 is a cell surface glycoprotein produced by the vascular endothelium, as well as on macrophage-like and dandritic cell types, in response to certain inflammatory stimuli.

VCAM-1 interacts with the integrin VLA-4 present on mononuclear leukocytes.

The cDNA for VCAM-1 was isolated by screening a cDNA library from IL-1β-activated human endothelial cells. Large quantities of the protein were expressed in insect cells using a baculovirus expression system. VCAM-1 expressing cells were shown to bind specifically to a variety of VLA-4 expressing cell lines (Jurkat. THP-1, U937).

Another reference on VCAM-1 is Expression and Functional Characterisation of Recombinant Human Vascular Cell Adhesion Molecule-1 (VCAM-1) Synthesised by Baculovirus-Infected Insect Cells. J. K. Stoltenborg, R. A. Straney, R. J. Tritch, W. M. Mackin and H. J. George, Protein Expression and Purification, 4 (1993) 585–593.

RPMI 1640—Cell media. Source Gibco BRL (Life technologies; Cat No 31870-025).

FCS—Foetal calf serum. Source Advanced protein products (West Midlands UK) Cat No AS-302-50.

BCECF-AM—2',7'-bis (2 carboxyethyl)-5-($\epsilon$6)-carboxyfluoroscein acetoxymethyl ester). source: Molecular Probes Inc USA; Cat No B-1150.

CHO DG44—Chinese hamster ovary cell line (ATCC derived; Reference: Som Cell Mol Gen 1986; 12; 555–666)

DMEM—Dulbecco's modified eagle medium. Source Gibco BRL (Life technologies, Cat No 41966–029.

Antibiotic—Penicillin-steptomycin. Source Gibco BRL (Life Technologies: Cat No 15070-022).

Fluorskan—is a fluorimeter.

HUVEC—Human umbilical cord endothelial cells. Primary cultures prepared from tissue samples. (Reference: J Clin Invest. 1973 52; 2745–2747.

Recombinant human TNFα—Tumor necrosis factor

Alzet osmotic minipump—Subcutaneous implanted micro osmotic pump, Alza Corporation Palo Alto, Calif.

2.1 MOLT-4 celit Fibronectin-VCAM-1 Adhesion Assay.

The MOLT-4 cell/Fibronectin-VCAM-1 adhesion assay is used to investigate the interaction of the integrin VLA4 (Very Late Antigen, α4/β1) expressed on the MOLT-4 cell membrane with fibronectin or recombinant soluble VCAM-1 (rsVCAM-1).

Fibronectin or rsVCAM-1 are coated overnight at 4° C. onto polystyrene 96-well microtitre plates at concentrations of 20 μg/ml and 1 μg/ml respectively. Following this, a concentrated BSA solution (10 mg/ml) is added to block non-specific binding sites. After aspiration of these solutions, equal volumes of compound and MOLT-4 cell suspension (1×10$^6$ cells/ml) are added. Adhesion takes place during a 2 hour incubation at 37° C., non or loosely adherent cells are removed by gentle agitation followed by vacuum aspiration. Quantitation of the remaining adherent cells is by means of a colorimetric assay of acid phosphatase activity, which is read on a spectrophotometer. Compounds which inhibit adhesion result in a lower absorbance reading. Standard, control and test conditions are assayed in triplicate, percentage inhibition being calculated with respect to total (no inhibitor) and non-specific (no fibronectin) standards on each plate.

2.2 Cell-Cell Assays 2.2.1. VCAM-1 CHO cells

MOLT-4 cells (RPMI 1640 supplemented with 5% FCS and 2 mM L-Glutamine) are labelled with the fluorescent dye BCECF-AM (301 g/ml per 3×10$^6$ cells). CHO DG44 transfected with full length VCAM-1 cDNA were selected for VCAM-1 expression by FACS analysis and grown to confluence in 96 well tissue culture plates. Prior to use in the adhesion assay CHO DG44 cells are washed three times (DMEM supplemented with 5% FCS, 2 mM L-Glutameine and 2% antibiotic). MOLT-4 ($10^5$ cell/well) cells are over laid on the VCAM-1 expressing CHO cells and incubated for 30 minutes at 37° C. 5% $CO_2$. The non-adherent cells are removed by washing the plate three times (RPMI 1640 supplemented with 5% FCS and 2 mM L-Glutamine) following which the plates are blotted dry on tissue paper. 100 μl of 2% Triton X-100is added to each well and the plates read using a Fluoroskan (excitation=485 nM, emission=538 nM). Compounds are dissolved in appropriate solvents and added to the MOLT-4 cells prior to addition to HUVEC cultures, inhibition of adhesion is calculated comparing level of adhesion (fluorescence) of control vehicle treated cells with compound treated cells.

2.2.2 Human Umbilical Vein Endothelial Cells.

MOLT-4 cells (RPMI 1640 supplemented with 5% FCS and 2 mM L-Glutamine) are labelled with the fluorescent dye BCECF-AM (30 μg/ml per $3\times10^6$cells). Primary HUVEC are grown to confluence in 96 well tissue culture plates and incubated for 18 hours with 2 U/ml recombinant human TNFα. Prior to use in the adhesion assay the primary HUVEC monolayers are washed (M199 supplemented with 5% FCS, 2 mM L-Glutactine and 2% antibiotic). MOLT-4 ($10^5$cell/well) cells are overlaid on the primary HUVEC and incubated for 30 minutes at 37° C. 5% $CO_2$. The non-adherent cells are removed by washing the plate three times (RPMI 1640 supplemented with 5% FCS and 2 mM L-Glutamine) and dried by blotting on tissue paper. 100 μl of 2% Triton X-100 is added to each well and the plates read using a Fluoroskan (excitation=485 nM, emission 538 nM). Compounds are dissolved in appropriate solvents and added to the MOLT-4 cells prior to addition to HUVEC cultures, inhibition of adhesion is calculated comparing level of adhesion (fluorescence) of control vehicle treated cells with compound treated cells.

2.3 In Vivo Contact hypersensitivity Response.

Balb/C male mice (20–25 g) are sensitised with oxazolone (50 μl of 0.24% in acetone/olive oil) by topical application to the shaved skin area of the back. Seven days later the mice are challenged by topical application of oxazolone (25 μl of 0.25% in acetone/olive oil) to the surface of the ear. Swelling of the ear develops over a 24 hour period following which ear thickness is measured and compared to the pre-challenge thickness, the percentage increase in ear thickness is calculated. Compounds are delivered via Alzet osmotic minipump daily dosing (once/day) which are implanted 24 hours prior to the oxazolone challenge, inhibition of the inflammatory response is calculated comparing vehicle treated animals and compound treated groups (n=6 animals per group).

2.4 In Vivo Ovalbumin Delayed type Hypersensitivity Model.

Balb/C female mice (20–25 g) are immunised on the flank with an emulsion of ovalbumin (Sigma, 0.1 ml subcutaneous injection of 2 mg/ml solution mixed (1:1) with complete Freunds adjuvant; Difco). Seven days later the mice are challenged by subplantar injection of ovalbumin (30 μl of 1% heat aggregated ovalbumin in saline) into the left hind foot pad. Swelling of the foot develops over a 24 hour period following which foot pad thickness is measured and compared to the pre-challenge thickness, the percentage increase in in foot pad thickness is calculated. Compounds are delivered via Alzet osmotic minipump daily dosing (once/day) which are implanted 24 hours prior to the ovalbumin challenge and the inhibition of the inflammatory response is calculated comparing vehicle treated animals and compound treated groups (n=5 animals per group).

2.5 In Vivo Antigen Induced Arthritis Model.

Mice are immunised and boosted 7 days later with a combination of 100 μg methylated BSA in complete Freund's adjuvant (s.c.) followed by an intraperitoneal injection of bordetella pertussis organisms. Two weeks after boost animals are challenged with 100 μg methylated-bovine serum albumin (BSA) intra-articularly and the degree of inflammation/arthritis determined by measuring knee joint swelling, histology and changes in acute phase proteins. Compounds are dosed for 7 to 14 days commencing the day prior to challenge and the degree of inflammation/arthritis compared with the control animals and contralateral knee.

2.6 Experimental Autoimmune Encephalomyelitis Model.

Disease induced by s.c. injection of a mixture of spinal cord homogenate, myelin basic protein (MBP) or encephalogenic peptides with complete Freund's adjuvant (CFA), coupled with an i.p. injection of pertussis toxin. For acute disease, pertussis injection is repeated 2 days after imrnmunisation. For chronic disease, pertussis is omitted and mice receive two injections of antigen in CFA, with an interval of 7 days. Disease is assessed by clinical scoring supported by histology. Compounds are dosed for 7 to 14 days commencing the day prior to challenge and the symptoms compared with the control animals.

TABLE 1

Synthesis and purification of cyclic dimeric peptides

| Comp. No. | Precursor | No. | End Product Cyclic Peptide | High Pressure Liquid Chromatography (HPLC)(Gradient system and time) |
|---|---|---|---|---|
| 17 | Ile-Leu-Asp(OBut)-Val-N⟨piperazine⟩N—CH₂COOH | 1 | Cyclic: OC-Ile-Leu-Asp-Val-N⟨piperazine⟩N—CH₂ / H₂C—N⟨piperazine⟩N-Val-Asp-Leu-Ile-CO | 20–50% water-acetonitrile (65 min.) |
| 18 | OR: CO-Ile-Leu-Asp(OBut)-Val-N⟨piperazine⟩N—CH₂ / CH₂—N⟨piperazine⟩N•Val-Asp(OBut)-Leu-Ile—HOOC | | | |
| 19 | D-Leu-Leu-Asp(OBut)-Val-N⟨piperazine⟩N—CH₂—HOOC | 2 | Cyclic: OC-D-Leu-Leu-Asp-Val-N⟨piperazine⟩N—CH₂ / H₂C—N⟨piperazine⟩N-Val-Asp-Leu-D-Leu-CO | 10–40% water-acetonitrile (60 min.) |
| 20 | Ile-Leu-Asp(OBut)-Val-N⟨piperazine⟩N—CH₂CH₂ / H₂C—N⟨piperazine⟩N-Val-Asp(OBut)-Leu-Ile-CO / CH₂—COOH | 3 | Cyclic: H₂C—CO-Ile-Leu-Asp-Val-N⟨piperazine⟩N—CH₂ / H₂C—N⟨piperazine⟩N-Val-Asp-Leu-Ile-CO—CH₂ | 10–50% water-acetonitrile (60 min.) |

TABLE 1-continued

Synthesis and purification of cyclic dimeric peptides

| Comp. No. | Precursor | No. | End Product Cyclic Peptide | High Pressure Liquid Chromatography (HPLC)(Gradient system and time) |
|---|---|---|---|---|
| 21 | b-Ala-Ile-Leu-Asp(OBut)-Val-N–CH₂CH₂<br>             \<br>              N-Val-Asp(OBut)-Leu-Ile-bAla-CO<br>             /<br>          N–CH₂—COOH | 4 | CH₂CO•bAla-Ile-Leu-Asp-Val-N–(piperazine)–CH₂<br>                                                       \<br>                                        N-Val-Asp-Leu-Ile-bAla-CO | 20–45% water-acetonitrile (65 min.) |
| 22 | b-Ala-Ile-Leu-Asp(OBut)-Val-N–(piperazine)–CH₂<br>                                          \<br>                                 N-Val-Asp(OBut)-Leu-Ile-OC<br>                                          /<br>                                    CH₂—COOH | 5 | (piperazine)N–CH₂<br>                     \<br>           CO-bAla-Ile-Leu-Asp-ValN<br>                                  \<br>                         N-Val-Asp-Leu-Ile-CO<br>                         /<br>                      CH₂ | 20–45% water-acetonitrile (65 min.) |
| 23 | D-Leu—Leu—Asp—Val—β-Ala-D-Leu—Leu—Asp—Val-β-Ala | 6 | OC——D-Leu-Leu-Asp-Val-NHCH₂——CH₂<br>                                                \<br>    CH₂——CH₂——NH-Val-Asp-Leu-D-Leu-CO | 10–50% water-acetonitrile (60 min.) |
| 24 | Asp(OBut)-Val-N–(piperidine)–CO-Ile-Leu | 7 | OC-Ile-Leu-Asp-Val-N–(piperidine)–N-Val-Asp-Leu-Ile-CO | 15–55% water-acetonitrile (65 min.) |

TABLE 1-continued

Synthesis and purification of cyclic dimeric peptides

| Comp. No. | Precursor | No. | End Product Cyclic Peptide | High Pressure Liquid Chromatography (HPLC)(Gradient system and time) |
|---|---|---|---|---|
| 25 | D-Arg(Pbf)—MeIle—Leu—Asp(OBut)—Val-D-Arg(Pbf)—MeIle—Leu—Asp—Val | 8 | c(MeIle—Leu—Asp—Val-D-Arg—MeIle—Leu—Asp-D-Arg) | Deltapak column 20–36% (80 min.) |
| 26 | D-Arg(Pbf)-D-Arg(Pbf)—MeIle—Leu—Asp(OBut)—Val-D-Arg(Pbf)-D-Arg(Pbf)—MeIle—Leu—Asp—Val | 9 | c(MeIle—Leu—Asp—Val-D-Arg-D-Arg—MeIle—Leu—Asp—Val-D-Arg-D-Arg) | Deltapak column 10–40% (80 min.) |
| 27 | D-Ala-D-Ala—MeIle—Leu—Asp(OBut)—Val-D-Arg(Pbf)—MeIle—Leu—Asp—Val | 10 | c(MeIle—Leu—Asp—Val-D-Arg-D-Ala-D-Ala—MeIle—Leu—Asp—Val-D-Ala-D-Ala) | Deltapak column 20–36% (80 min.) |
| 28 | MeIle-Leu-Asp(OBut)-Val-N[piperazine]N-Val-Asp(OBut)-Leu-MeIle-CO, CH₂—COOH | 11 | OC-MeIle-Leu-Asp-Val-N[piperazine]N-Val-Asp-Leu-MeIle-CO | Deltapak column 20–40% (80 min.) |
| 29 | MePhe-Leu-Asp(OBut)-Val-N[piperazine]N-Val-Asp(OBut)-Leu-MePhe-CO, CH₂—COOH | 12 | OC-MePhe-Leu-Asp-Val-N[piperazine]N-Val-Asp-Leu-MePhe-CO | Deltapak column 20–45% (80 min.) |
| 30 | D-Arg(Pbf)-MePhe-Leu-Asp(OBut)-Val-N[piperazine]N-Val-Asp(OBut)-Leu-MePhe-D-Arg(Pbf)CO, CH₂—COOH | 13 | OC-D-Arg-MePhe-Leu-Asp-Val-N[piperazine]N-Val-Asp-Leu-MePhe-D-Arg-CO | Deltapak column 20–30% (60 min.) |

TABLE 1-continued

Synthesis and purification of cyclic dimeric peptides

| Comp. No. | Precursor | No. | End Product Cyclic Peptide | High Pressure Liquid Chromatography (HPLC)(Gradient system and time) |
|---|---|---|---|---|
| 31 | 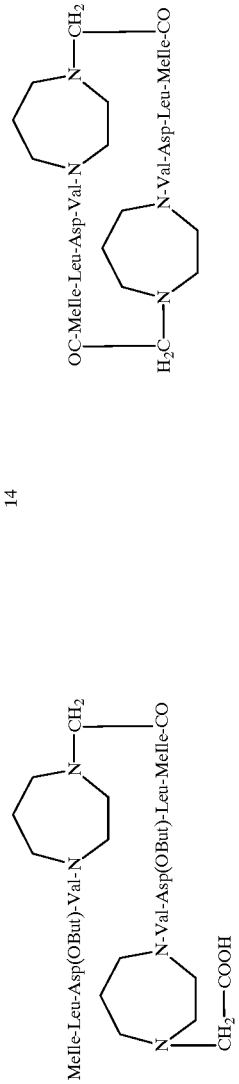 MeIle-Leu-Asp(OBut)-Val-N<br>N-Val-Asp(OBut)-Leu-MeIle-CO<br>CH₂—COOH | 14 | 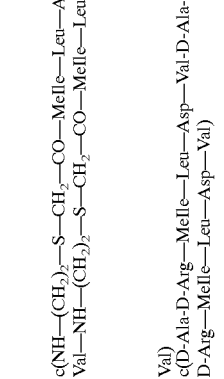 OC-MeIle-Leu-Asp-Val-N<br>N-Val-Asp-Leu-MeIle-CO | Deltapak column 20–45% (80 min.) |
| 32 | NH₂(CH₂)₂—S—CH₂—CO—MeIle—Leu—Asp(OBut)—Val—NH—(CH₂)₂—S—CH₂—CO—MeIle—Leu—Asp(OBut)—Val | 15 | c(NH—(CH₂)₂—S—CH₂—CO—MeIle—Leu—Asp—Val—NH—(CH₂)₂—S—CH₂—CO—MeIle—Leu—Asp—Val) | Deltapak column 30–70% (80 min.) |
| 33 | D-Ala-D-Arg(Pbf)—MeIle—Leu—Asp(OBut)—Val-D-Ala-D-Arg(Pbf)—MeIle—Leu—Asp(OBut)—Val | 16 | c(D-Ala-D-Arg—MeIle—Leu—Asp—Val-D-Ala-D-Arg—MeIle—Leu—Asp—Val) | Deltapak column 20–36% (80 min.) |

Preparative HPLC was carried out using a reverse phase ($C_{18}$) 1 inch diameter Vydac column (218TP1022, 22 × 250 mm) or a Deltapak (30 × 300 mm) column. The solvent system consisted of water and acetonitrile (each containing 0.1% trifluoroacetic acid). The column was eluted using gradient (solvent ratio and time shown in the table) with increasing concentrations of acetonitrile run at a rate of 10 ml/minute. The flow rate on the Deltapak column was 30 ml/min.

TABLE 2

Characterisation of the Cyclic Dimeric Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M + H)+ |
|---|---|---|---|---|
| 1 | OC-Ile-Leu-Asp-Val-N(piperazine)N—CH₂ / H₂C—N(piperazine)N-Val-Asp-Leu-Ile-CO | Asp 2.03, Val 1.95, Ile 1.97, Leu 2.01 | 21.76 10–60% (30 min.) | 1133.6 |
| 2 | OC—D-Leu-Leu-Asp-Val·N(piperazine)N—CH₂ / H₂C—N(piperazine)N-Val-Asp-Leu-D-Leu-CO | Asp 2.05, Val 1.98, Ile 1.98, Leu 2.01 | 22.46 10–60% (30 min.) | 1133.8 |
| 3 | H₂C—CO-Ile-Leu-Asp-Val-N(piperazine)N—CH₂ / H₂C—N(piperazine)N-Val-Asp-Leu-Ile-CO—CH₂ | Asp 2.0, Val 1.96, Ile 1.90, Leu 1.96. | 17.5 20–80% (40 min.) | 1161.7 |
| 4 | CH₂CO·bAla-Ile-Leu-Asp-Val-N(piperidine) / N-Val-Asp-Leu-Ile-bAla-CO—CH₂(piperidine) | Asp 1.01, Val 0.98, Ile 0.98, Leu 1.02, β-Ala 0.99 | 21.23 10–60% (30 min.) | [M + 2H]²⁺ 638.7 |
| 5 | CO-bAla-Ile-Leu-Asp-Val·N(piperazine)N / CH₂ ... N-Val-Asp-Leu-Ile-CO CH₂ | Asp 2.02, Val 1.98, Ile 1.94, Leu 2.06, β-Ala 0.95 | 21.43 10–60% (30 min.) | [M + 2H]²⁺ 603.0 |
| 6 | OC—D-Leu-Leu-Asp-Val-NHCH₂—CH₂ / CH₂—CH₂—NH-Val-Asp-Leu-D-Leu-CO | Asp 2.10, Val 2.10, Leu 4.0, β-Ala 1.92 | 19.53 10–80% (30 min.) | 1023.7 |
| 7 | OC-Ile-Leu-Asp-Val-N(piperidine) / N-Val-Asp-Leu-Ile-CO(piperidine) | Asp 0.98, Val 0.96, Ile 0.96, Leu 1.05 | 30.2 10–60% (30 min.) | 1104 |
| 8 | c(MeIle—Leu—Asp—Val-D-Arg—MeIle—Leu—Asp—Val-D-Arg) | Asp 1.02, Val 0.96, Leu 1.02, Arg 1.01. | 29.60 20–45% (30 min.) | 1221.9 (M + 2H)²⁺ = 611.7 |
| 9 | c(MeIle—Leu—Asp—Val-D-Arg-D-Arg—MeIle—Leu—Asp—Val-D-Arg-D-Arg) | Asp 1.03, Val 1.01, Leu 1.03, Arg 1.94. | 25.97 10–40% (30 min.) | (M + 2H)²⁺ = 767.8 |
| 10 | c(MeIle—Leu—Asp—Val-D-Arg-D-Arg—MeIle—Leu—Asp—Val-D-Ala-D-Ala) | Asp 1.00, Ala 1.02, Val 0.95, Leu 1.01, Arg 1.01. | 24.61 20–45% (30 min.) | 1363.9 (M + 2H)²⁺ = 682.8 |

TABLE 2-continued

Characterisation of the Cyclic Dimeric Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy $(M + H)^+$ |
|---|---|---|---|---|
| 11 | OC-MeIle-Leu-Asp-Val-N / N—CH$_2$ ; H$_2$C—N / N-Val-Asp-Leu-MeIle-CO (piperazine linker) | Asp 0.98, Val 1.01, Leu 1.01 | 29.68 10–40% (30 min.) | 1161.7 |
| 12 | OC-MePhe-Leu-Asp-Val-N / N—CH$_2$ ; H$_2$C—N / N-Val-Asp-Leu-MePhe-CO (piperazine linker) | Asp 1.02, Val 0.96, Leu 1.02 | 28.27 10–60% (30 min.) | 1229.9 $(M + 2H)^{2+}$ = 615.7 |
| 13 | OC—D-Arg-MePhe-Leu-Asp-Val-N / N—CH$_2$ ; H$_2$C—N / N-Val-Asp-Leu-MePhe-D-Arg-CO (piperazine linker) | Asp 1.03, Val 0.96, Leu 1.02, Arg 0.99. | 24.01 10–60% (30 min.) | $(M + 2H)^{2+}$ 771.8 |
| 14 | OC-MeIle-Leu-Asp-Val-N / N—CH$_2$ ; H$_2$C—N / N-Val-Asp-Leu-MeIle-CO (homopiperazine/diazepane linker) | Asp 1.02, Val 0.95, Leu 1.03. | 25.54 20–45% (30 min.) | $(M + 2H)^{2+}$ = 595.8 |
| 15 | c(NH—(CH$_2$)$_2$—S—CH$_2$—CO—MeIle—Leu—Asp—Val—NH—(CH$_2$)$_2$—S—CH$_2$—CO—MeIle—Leu—Asp—Val) | Asp 1.03, Val 0.96, Leu 1.02. | 21.53 30–70% (30 min.) | 1143.7 |
| 16 | c(D-Ala-D-Arg—MeIle—Leu—Asp—Val-D-Ala-D-Arg—MeIle—Leu—Asp—Val) | Asp 1.02, Ala 1.03, Val 0.97, Leu 1.0, Arg 1.02. | 25.38 20–45% (30 min.) | 1364.1 $(M + 2H)^{2+}$ = 682.5 |

Analytical HPLC was carried out using either a reverse phase (C$_{18}$) Vydac column (218TP54, 4.6 × 250 mm) or a Novapak column (3.9 × 150 mm). Unless otherwise stated in the above table a Vydac column was used for the compound. The solvent system consisted of water and acetonitrile (each containing 0.1% trifluoroacetic acid). The column was eluted using a gradient (solvent ratio and time shown in the table) with increasing concentrations of acetonitrile run at a rate of 1 ml/minute.

The following data gives the sequence listing generated using the patentin software which has to be provided for some patent offices.

All compounds in the following listing are represented diagramatically in Tables 1 and 2.

I claim:

1. A cyclic dimeric peptide of formula 1

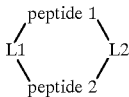

Formula 1 wherein peptide 1 and peptide 2 independently represent a tetrapeptide of formula -AA1-AA2-AA3-AA4- juxtaposed in parallel or antiparallel orientation; and AA1 is an L or D amino acid selected from Ile, Leu, Pro, Gly, Tic, Gln, and Phe;

AA2 is an L amino acid selected from Leu, Ile, Phe, Pro and Val;

AA3 is an L amino acid selected from Asp and Glu;

AA4 is an L amino acid selected from Val, Leu, Ile, Phe, Ser, Pro and Cha;

L1 and L2 independently represent linking moieties for linking peptides 1 and 2 to form a cyclic peptide; or a salt thereof, wherein AA1 to AA4 each have the general formula 2

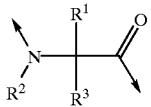

Formula 2 wherein $R^1$ is the amino acid side chain and $R^2$ and $R^3$ are independently selected from H and $C_{1-4}$ alkyl.

2. A cyclic dimeric peptide according to claim 1 wherein AA1 is selected from Ile, D-Leu MeIle and MePhe; AA2 is Leu; AA3 is Asp; and AA4 is Val or a salt thereof.

3. A cyclic dimeric peptide according to any one of claims 1 and 2 wherein the peptides 1 and 2 are in antiparallel juxtaposition or a salt thereof.

4. A cyclic dimeric peptide according to claim 3 wherein L1 and L2 are independently selected from a group of formula

—N($R^4$)—X—C(O)— wherein:

$R^4$ is selected from H and $C_{1-4}$ alkyl, X represents —$(CH_2)_n$— wherein n=1–4, optionally substituted on —$CH_2$ with $C_{1-4}$ alkyl or $NH_2$; or X and $NR^4$ together represent a group of

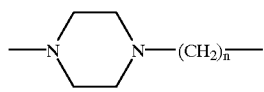

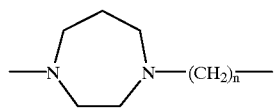

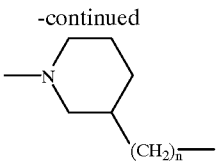

in which n=0–4; or a salt thereof.

5. A cyclic dimeric peptide according to claim 3 wherein L1 and L2 have a formula independently selected from the group consisting of:

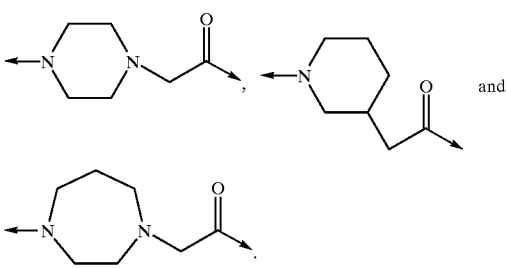

6. A cyclic dimeric peptide according to claim 3 wherein L1 and L2 have a formula independently selected from the group consisting of:

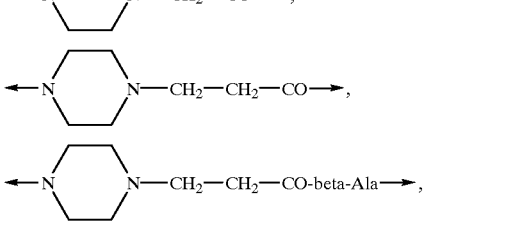

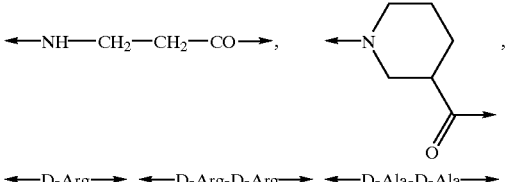

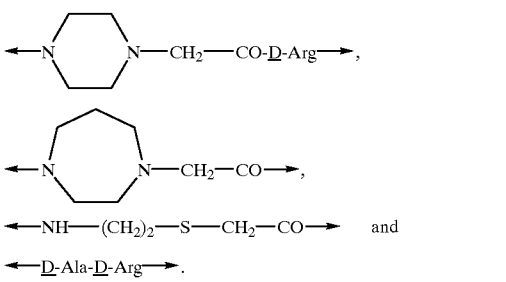

7. A cyclic dimeric peptide according to claim 6 wherein L1 and L2 have a formula independently selected from the group consisting of:

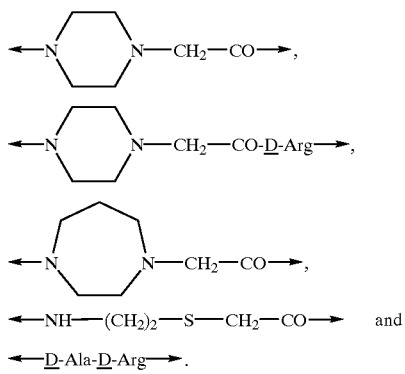

8. A cyclic dimeric peptide according to any one of claims 1 and 2 in which L1 and L2 are identical.

9. A cyclic dimeric peptide selected from

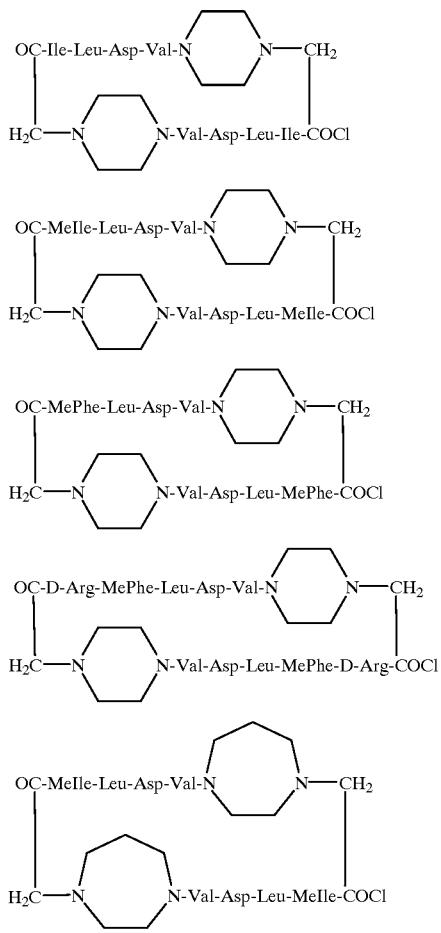

or a salt thereof.

10. A process for the manufacture of a cyclic dimeric peptide of formula 1

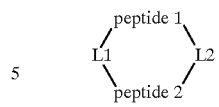

Formula 1 wherein peptide 1 and peptide 2 independently represent a tetrapeptide of formula -AA1-AA2-AA3-AA4- juxtaposed in parallel or antiparallel orientation; and AA1 is an L or D amino acid selected from Ile, Leu, Pro, Gly, Tic, Gln, and Phe;

AA2 is an L amino acid selected from Leu, Ile, Phe, Pro and Val;

AA3 is an L amino acid selected from Asp and Glu;

AA4 is an L amino acid selected from Val, Leu, Ile, Phe, Ser, Pro and Cha;

L1 and L2 independently represent linking moieties for linking peptides 1 and 2 to form a cyclic peptide; or a salt thereof, wherein AA1 to AA4 each have the general formula 2

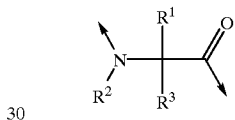

Formula 2 wherein R1 is the amino acid side chain and R2 and R3 are independently selected from H and C1–4 alkyl: selected from:

(a) removing one or more conventional peptide protecting groups from a protected polypeptide of formula 10:

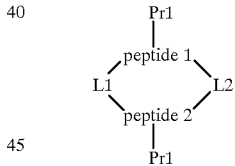

Formula 10 wherein Pr1 is a protecting group on the acid group in the side chain of AA3, to give a cyclic peptide polypeptide of the formula 1;

and, optionally, simultaneously or subsequently, also removing any additional conventional peptide protecting groups and optionally converting the product thus obtained into a salt thereof; and (b) coupling peptide one to peptide 2, via linkers L1 and L2 by forming amide bonds between the carboxylic acid group, or a reactive derivative thereof on each said peptide with an amino group on a linker, and between the amino group on each said peptide with a carboxylic acid group on a linker, such that a protected or unprotected cyclic peptide having the sequence indicated in formula 1 is produced and, if necessary, removing any protecting groups using process (a) above and optionally converting the product thus obtained into a salt thereof.

11. A pharmaceutical composition comprising a cyclic dimeric peptide according to any one of claims 1 and 3 or a salt thereof in association with a pharmaceutically acceptable diluent or carrier.

12. A pharmaceutical composition according to claim 11 for parenteral administration designed for slow release over a period of at least five days.

13. A method for treating a disease or medical condition mediated by the interaction of VCAM-1 and the integrin receptor VLA-4, wherein said method comprises administering to a patient in need thereof, an effective amount of a cyclic dimeric peptide according to any one of claims 1 and 2 or a pharmaceutically acceptable salt thereof.

14. A method for inhibiting the interaction between VCAM-1 and/or fibronectin and the integrin receptor VLA-4 in mammals in need of such treatment comprising administering to said mammals an effective amount of a cyclic dimeric peptide according to any one of claims 1 and 3 or a pharmaceutically acceptable salt thereof.

15. A method according to claim 14 wherein the mammal in need of treatment is suffering from multiple sclerosis asthma or rheumatoid arthritis.

16. A method for treating a disease or medical condition mediated by the interaction of VCAM-1 and the integrin receptor VLA-4, wherein said method comprises administering to a patient in need thereof, an effective amount of a cyclic dimeric peptide of the formula 1

Formula 1

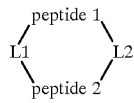

or a pharmaceutically-acceptable salt thereof;

wherein peptide 1 and peptide 2 independently represent a tetrapeptide of formula -AA1-AA2-AA3-AA4- juxtaposed in parallel or antiparallel orientation; and AA1 is an L or D amino acid selected from Ile, Leu, Pro, Gly, Tic, Gln, and Phe;

AA2 is an L amino acid selected from Leu, Ile, Phe, Pro and Val;

AA3 is an L amino acid selected from Asp and Glu;

AA4 is an L amino acid selected from Val, Leu, Ile, Phe, Ser. Pro and Cha;

L1 and L2 independently represent linking moieties for linking peptides 1 and 2 to form a cyclic peptide; or a salt thereof, wherein AA1 to AA4 each have the general formula 2

Formula 2

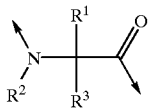

wherein R1 is the amino acid side chain and R2 and R3 are independently selected from H and $C_{1-4}$ alkyl.

* * * * *

```
                    SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
        (A) LENGTH: 10 amino acids
        (B) TYPE: amino acid
        (C) STRANDEDNESS: single
        (D) TOPOLOGY: circular
```

```
         (ii) MOLECULE TYPE: peptide (ix) FEATURE:
              (A) NAME/KEY: Peptide
              (B) LOCATION:5
              (D) OTHER INFORMATION:/product= "OTHER"
                  /note= "PIPERAZINYL-1-YL-ACETYL"

(ix) FEATURE:
              (A) NAME/KEY: Peptide
              (B) LOCATION:10
              (D) OTHER INFORMATION:/product= "OTHER"
                  /note= "PIPERAZINYL-1-YL-ACETYL"

(xi) SEQUENCE DESCRIPTION: SEQ ID NO: 1:

Ile Leu Asp Val Xaa Ile Leu Asp Val Xaa
1               5                   10

(2) INFORMATION FOR SEQ ID NO: 2:

(i) SEQUENCE CHARACTERISTICS:
              (A) LENGTH: 10 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:1
              (D) OTHER INFORMATION:/product= "OTHER"
                  /note= "D-LEU"

(ix) FEATURE:
              (A) NAME/KEY: Peptide
              (B) LOCATION:5
              (D) OTHER INFORMATION:/product= "OTHER"
                  /note= "PIPERAZINYL-1-YL-ACETYL"

(ix) FEATURE:
              (A) NAME/KEY: Peptide
              (B) LOCATION:6
              (D) OTHER INFORMATION:/product= "OTHER"
                  /note= "D-LEU"

(ix) FEATURE:
              (A) NAME/KEY: Peptide
              (B) LOCATION:10
              (D) OTHER INFORMATION:/product= "OTHER"
                  /note= "PIPERAZINYL-1-YL-ACETYL"

(xi) SEQUENCE DESCRIPTION: SEQ ID NO: 2:

Xaa Leu Asp Val Xaa Xaa Leu Asp Val Xaa
1               5                   10

(2) INFORMATION FOR SEQ ID NO: 3:

(i) SEQUENCE CHARACTERISTICS:
              (A) LENGTH: 10 amino acids
              (B) TYPE: amino acid
              (C) STRANDEDNESS: single
              (D) TOPOLOGY: circular (ii) MOLECULE TYPE: peptide (ix) FEATURE:
              (A) NAME/KEY: Peptide
              (B) LOCATION:5
              (D) OTHER INFORMATION:/product= "OTHER"
                  /note= "PIPERAZINYL-1-YL-PROPIONYL"

(ix) FEATURE:
              (A) NAME/KEY: Peptide
              (B) LOCATION:10
```

```
            (D) OTHER INFORMATION:/product= "OTHER"
                /note= "PIPERAZINYL-1-YL-PROPIONYL"

(xi) SEQUENCE DESCRIPTION: SEQ ID NO: 3:

Ile Leu Asp Val Xaa Ile Leu Asp Val Xaa
1               5                  10

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "bAla"

(ix) FEATURE:
        (A) NAME/KEY: Peptide
        (B) LOCATION:6
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:7
        (D) OTHER INFORMATION:/product= "bAla"

(ix) FEATURE:
        (A) NAME/KEY: Peptide
        (B) LOCATION:12
        (D) OTHER INFORMATION:/product= "OTHER"
            /note= "PIPERAZINYL-1-YL-ACETYL"

(xi) SEQUENCE DESCRIPTION: SEQ ID NO: 4:

Ala Ile Leu Asp Val Xaa Ala Ile Leu Asp Val Xaa
1               5                  10

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "bAla"

(ix) FEATURE:
        (A) NAME/KEY: Peptide
        (B) LOCATION:6
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:11
        (D) OTHER INFORMATION:/product= "OTHER"
            /note= "PIPERAZINYL-1-YL-ACETYL"

(xi) SEQUENCE DESCRIPTION: SEQ ID NO: 5:

Ala Ile Leu Asp Val Xaa Ile Leu Asp Val Xaa
1               5                  10
```

```
(2) INFORMATION FOR SEQ ID NO: 6:

(i) SEQUENCE CHARACTERISTICS:
        (A) LENGTH: 10 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "D-Leu"

(ix) FEATURE:
        (A) NAME/KEY: Peptide
        (B) LOCATION:5
        (D) OTHER INFORMATION:/product= "OTHER"
            /note= "-NH-CH2-CH2-CO-"

(ix) FEATURE:
        (A) NAME/KEY: Peptide
        (B) LOCATION:6
        (D) OTHER INFORMATION:/product= "OTHER"
            /note= "D-LEU"

(ix) FEATURE:
        (A) NAME/KEY: Peptide
        (B) LOCATION:10
        (D) OTHER INFORMATION:/product= "OTHER"
            /note= "-NH-CH2-CH2-CO-"

(xi) SEQUENCE DESCRIPTION: SEQ ID NO: 6:

Xaa Leu Asp Val Xaa Xaa Leu Asp Val Xaa
1               5                   10

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:5
        (D) OTHER INFORMATION:/product= "OTHER"
            /note= "PIPERIDYL-5-ACETYL"

(ix) FEATURE:
        (A) NAME/KEY: Peptide
        (B) LOCATION:10
        (D) OTHER INFORMATION:/product= "OTHER"
            /note= "PIPERIDYL-5-ACETYL"

(xi) SEQUENCE DESCRIPTION: SEQ ID NO: 7:

Ile Leu Asp Val Xaa Ile Leu Asp Val Xaa
1               5                   10

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: circular (ii) MOLECULE TYPE: peptide
```

```
        (ix) FEATURE:
             (A) NAME/KEY: Peptide
             (B) LOCATION:1
             (D) OTHER INFORMATION:/product= "MeIle"

(ix) FEATURE:
             (A) NAME/KEY: Peptide
             (B) LOCATION:5
             (D) OTHER INFORMATION:/product= "OTHER"
                 /note= "D-Arg"

(ix) FEATURE:
             (A) NAME/KEY: Peptide
             (B) LOCATION:6
             (D) OTHER INFORMATION:/product= "MeIle"

(ix) FEATURE:
             (A) NAME/KEY: Peptide
             (B) LOCATION:10
             (D) OTHER INFORMATION:/product= "OTHER"
                 /note= "D-Arg"

(xi) SEQUENCE DESCRIPTION: SEQ ID NO: 8:

Ile Leu Asp Val Xaa Ile Leu Asp Val Xaa
1               5                   10

(2) INFORMATION FOR SEQ ID NO: 9:

(i) SEQUENCE CHARACTERISTICS:
             (A) LENGTH: 12 amino acids
             (B) TYPE: amino acid
             (C) STRANDEDNESS: single
             (D) TOPOLOGY: circular (ii) MOLECULE TYPE: peptide (ix) FEATURE:
             (A) NAME/KEY: Peptide
             (B) LOCATION:1
             (D) OTHER INFORMATION:/product= "MeIle"

(ix) FEATURE:
             (A) NAME/KEY: Peptide
             (B) LOCATION:5
             (D) OTHER INFORMATION:/product= "OTHER"
                 /note= "D-Arg"

(ix) FEATURE:
             (A) NAME/KEY: Peptide
             (B) LOCATION:6
             (D) OTHER INFORMATION:/product= "OTHER"
                 /note= "D-Arg"

(ix) FEATURE:
             (A) NAME/KEY: Peptide
             (B) LOCATION:7
             (D) OTHER INFORMATION:/product= "MeIle"

(ix) FEATURE:
             (A) NAME/KEY: Peptide
             (B) LOCATION:11
             (D) OTHER INFORMATION:/product= "OTHER"
                 /note= "D-Arg"

(ix) FEATURE:
             (A) NAME/KEY: Peptide
             (B) LOCATION:12
             (D) OTHER INFORMATION:/product= "OTHER"
                 /note= "D-Arg"

(xi) SEQUENCE DESCRIPTION: SEQ ID NO: 9:

Ile Leu Asp Val Xaa Xaa Ile Leu Asp Val Xaa Xaa
1               5                   10

(2) INFORMATION FOR SEQ ID NO: 10:
```

(i) SEQUENCE CHARACTERISTICS:
            (A) LENGTH: 12 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "MeIle"

(ix) FEATURE:
            (A) NAME/KEY: Peptide
            (B) LOCATION:5
            (D) OTHER INFORMATION:/product= "OTHER"
                /note= "D-Arg"

(ix) FEATURE:
            (A) NAME/KEY: Peptide
            (B) LOCATION:6
            (D) OTHER INFORMATION:/product= "OTHER"
                /note= "D-Arg"

(ix) FEATURE:
            (A) NAME/KEY: Peptide
            (B) LOCATION:7
            (D) OTHER INFORMATION:/product= "MeIle"

(ix) FEATURE:
            (A) NAME/KEY: Peptide
            (B) LOCATION:11
            (D) OTHER INFORMATION:/product= "OTHER"
                /note= "D-Ala"

(ix) FEATURE:
            (A) NAME/KEY: Peptide
            (B) LOCATION:12
            (D) OTHER INFORMATION:/product= "OTHER"
                /note= "D-Ala"

(xi) SEQUENCE DESCRIPTION: SEQ ID NO: 10:

Ile Leu Asp Val Xaa Xaa Ile Leu Asp Val Xaa Xaa
1               5                   10

(2) INFORMATION FOR SEQ ID NO: 11:

(i) SEQUENCE CHARACTERISTICS:
            (A) LENGTH: 10 amino acids
            (B) TYPE: amino acid
            (C) STRANDEDNESS: single
            (D) TOPOLOGY: circular (ii) MOLECULE TYPE: peptide (ix) FEATURE:
            (A) NAME/KEY: Peptide
            (B) LOCATION:1
            (D) OTHER INFORMATION:/product= "MeIle"

(ix) FEATURE:
            (A) NAME/KEY: Peptide
            (B) LOCATION:5
            (D) OTHER INFORMATION:/product= "OTHER"
                /note= "PIPERAZINYL-1-YL-ACETYL"

(ix) FEATURE:
            (A) NAME/KEY: Peptide
            (B) LOCATION:6
            (D) OTHER INFORMATION:/product= "MeIle"

(ix) FEATURE:
            (A) NAME/KEY: Peptide
            (B) LOCATION:10
            (D) OTHER INFORMATION:/product= "OTHER"

/note= "PIPERAZINYL-1-YL-ACETYL"

(xi) SEQUENCE DESCRIPTION: SEQ ID NO: 11:

Ile Leu Asp Val Xaa Ile Leu Asp Val Xaa
1               5                   10

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "MePhe"

(ix) FEATURE:
        (A) NAME/KEY: Peptide
        (B) LOCATION:5
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:6
        (D) OTHER INFORMATION:/product= "OTHER"
            /note= "MePhe"

(ix) FEATURE:
        (A) NAME/KEY: Peptide
        (B) LOCATION:10
        (D) OTHER INFORMATION:/product= "OTHER"
            /note= "PIPERAZINYL-1-YL-ACETYL"

(xi) SEQUENCE DESCRIPTION: SEQ ID NO: 12:

Xaa Leu Asp Val Xaa Xaa Leu Asp Val Xaa
1               5                   10

(2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Peptide
        (B) LOCATION:1
        (D) OTHER INFORMATION:/product= "OTHER"
            /note= "D-Arg"

(ix) FEATURE:
        (A) NAME/KEY: Peptide
        (B) LOCATION:2
        (D) OTHER INFORMATION:/product= "OTHER"
            /note= "MePhe"

(ix) FEATURE:
        (A) NAME/KEY: Peptide
        (B) LOCATION:6
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:7

```
          (D) OTHER INFORMATION:/product= "OTHER"
              /note= "D-Arg"

(ix) FEATURE:
          (A) NAME/KEY: Peptide
          (B) LOCATION:8
          (D) OTHER INFORMATION:/product= "OTHER"
              /note= "MePhe"

(ix) FEATURE:
          (A) NAME/KEY: Peptide
          (B) LOCATION:12
          (D) OTHER INFORMATION:/product= "OTHER"
              /note= "PIPERAZINYL-1-YL-ACETYL"

(xi) SEQUENCE DESCRIPTION: SEQ ID NO: 13:

Xaa Xaa Leu Asp Val Xaa Xaa Xaa Leu Asp Val Xaa
1               5                   10

(2) INFORMATION FOR SEQ ID NO: 14:

(i) SEQUENCE CHARACTERISTICS:
          (A) LENGTH: 10 amino acids
          (B) TYPE: amino acid
          (C) STRANDEDNESS: single
          (D) TOPOLOGY: circular (ii) MOLECULE TYPE: peptide (ix) FEATURE:
          (A) NAME/KEY: Peptide
          (B) LOCATION:1
          (D) OTHER INFORMATION:/product= "MeIle"

(ix) FEATURE:
          (A) NAME/KEY: Peptide
          (B) LOCATION:5
          (D) OTHER INFORMATION:/product= "OTHER"
              /note= "1,4-DIAZEPAN-1-YL-ACETYL"

(ix) FEATURE:
          (A) NAME/KEY: Peptide
          (B) LOCATION:6
          (D) OTHER INFORMATION:/product= "MeIle"

(ix) FEATURE:
          (A) NAME/KEY: Peptide
          (B) LOCATION:10
          (D) OTHER INFORMATION:/product= "OTHER"
              /note= "1,4-DIAZEPAN-1-YL-ACETYL"

(xi) SEQUENCE DESCRIPTION: SEQ ID NO: 14:

Ile Leu Asp Val Xaa Ile Leu Asp Val Xaa
1               5                   10

(2) INFORMATION FOR SEQ ID NO: 15:

(i) SEQUENCE CHARACTERISTICS:
          (A) LENGTH: 10 amino acids
          (B) TYPE: amino acid
          (C) STRANDEDNESS: single
          (D) TOPOLOGY: circular (ii) MOLECULE TYPE: peptide (ix) FEATURE:
          (A) NAME/KEY: Peptide
          (B) LOCATION:1
          (D) OTHER INFORMATION:/product= "MeIle"

(ix) FEATURE:
          (A) NAME/KEY: Peptide
          (B) LOCATION:5
          (D) OTHER INFORMATION:/product= "OTHER"
              /note= "-NH-(CH2)2-S-CH2-CO-"
```

```
     (ix) FEATURE:
           (A) NAME/KEY: Peptide
           (B) LOCATION:6
           (D) OTHER INFORMATION:/product= "MeIle"

(ix) FEATURE:
           (A) NAME/KEY: Peptide
           (B) LOCATION:10
           (D) OTHER INFORMATION:/product= "OTHER"
               /note= "-NH-(CH2)2-S-CH2-CO-"

(xi) SEQUENCE DESCRIPTION: SEQ ID NO: 15:

Ile Leu Asp Val Xaa Ile Leu Asp Val Xaa
1               5                   10

(2) INFORMATION FOR SEQ ID NO: 16:

(i) SEQUENCE CHARACTERISTICS:
           (A) LENGTH: 12 amino acids
           (B) TYPE: amino acid
           (C) STRANDEDNESS: single
           (D) TOPOLOGY: circular (ii) MOLECULE TYPE: peptide (ix) FEATURE:
           (A) NAME/KEY: Peptide
           (B) LOCATION:1
           (D) OTHER INFORMATION:/product= "OTHER"
               /note= "D-Ala"

(ix) FEATURE:
           (A) NAME/KEY: Peptide
           (B) LOCATION:2
           (D) OTHER INFORMATION:/product= "OTHER"
               /note= "D-Arg"

(ix) FEATURE:
           (A) NAME/KEY: Peptide
           (B) LOCATION:3
           (D) OTHER INFORMATION:/product= "MeIle"

(ix) FEATURE:
           (A) NAME/KEY: Peptide
           (B) LOCATION:7
           (D) OTHER INFORMATION:/product= "OTHER"
               /note= "D-Ala"

(ix) FEATURE:
           (A) NAME/KEY: Peptide
           (B) LOCATION:8
           (D) OTHER INFORMATION:/product= "OTHER"
               /note= "D-Arg"

(ix) FEATURE:
           (A) NAME/KEY: Peptide
           (B) LOCATION:9
           (D) OTHER INFORMATION:/product= "MeIle"

(xi) SEQUENCE DESCRIPTION: SEQ ID NO: 16:

Xaa Xaa Ile Leu Asp Val Xaa Xaa Ile Leu Asp Val
1               5                   10

(2) INFORMATION FOR SEQ ID NO: 17:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (ix) FEATURE:
```

(A) NAME/KEY: Peptide
       (B) LOCATION:3
       (D) OTHER INFORMATION:/product= "OTHER"
           /note= "Asp(OBut)"

(ix) FEATURE:
       (A) NAME/KEY: Peptide
       (B) LOCATION:5
       (D) OTHER INFORMATION:/product= "OTHER"
           /note= "PIPERAZINYL-1-YL-ACETIC ACID"

(xi) SEQUENCE DESCRIPTION: SEQ ID NO: 17:

Ile Leu Xaa Val Xaa
1               5

(2) INFORMATION FOR SEQ ID NO: 18:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION:3
       (D) OTHER INFORMATION:/product= "OTHER"
           /note= "Asp(OBut)"

(ix) FEATURE:
       (A) NAME/KEY: Peptide
       (B) LOCATION:5
       (D) OTHER INFORMATION:/product= "OTHER"
           /note= "PIPERAZINYL-1-YL-ACETYL"

(ix) FEATURE:
       (A) NAME/KEY: Peptide
       (B) LOCATION:8
       (D) OTHER INFORMATION:/product= "OTHER"
           /note= "Asp(OBut)"

(ix) FEATURE:
       (A) NAME/KEY: Peptide
       (B) LOCATION:10
       (D) OTHER INFORMATION:/product= "OTHER"
           /note= "PIPERAZINYL-1-YL-ACETIC ACID"

(xi) SEQUENCE DESCRIPTION: SEQ ID NO: 18:

Ile Leu Xaa Val Xaa Ile Leu Xaa Val Xaa
1               5                   10

(2) INFORMATION FOR SEQ ID NO: 19:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION:1
       (D) OTHER INFORMATION:/product= "OTHER"
           /note= "D-Leu"

(ix) FEATURE:
       (A) NAME/KEY: Peptide
       (B) LOCATION:3
       (D) OTHER INFORMATION:/product= "OTHER"
           /note= "Asp(OBut)"

```
    (ix) FEATURE:
         (A) NAME/KEY: Peptide
         (B) LOCATION:5
         (D) OTHER INFORMATION:/product= "OTHER"
             /note= "PIPERAZINYL-1-YL-ACETIC ACID"

(xi) SEQUENCE DESCRIPTION: SEQ ID NO: 19:

Xaa Leu Xaa Val Xaa
1               5

(2) INFORMATION FOR SEQ ID NO: 20:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:3
         (D) OTHER INFORMATION:/product= "OTHER"
             /note= "Asp(OBut)"

(ix) FEATURE:
         (A) NAME/KEY: Peptide
         (B) LOCATION:5
         (D) OTHER INFORMATION:/product= "OTHER"
             /note= "PIPERAZINYL-1-YL-PROPIONYL"

(ix) FEATURE:
         (A) NAME/KEY: Peptide
         (B) LOCATION:8
         (D) OTHER INFORMATION:/product= "OTHER"
             /note= "Asp(OBut)"

(ix) FEATURE:
         (A) NAME/KEY: Peptide
         (B) LOCATION:10
         (D) OTHER INFORMATION:/product= "OTHER"
             /note= "PIPERAZINYL-1-YL-PROPIONIC ACID"

(xi) SEQUENCE DESCRIPTION: SEQ ID NO: 20:

Ile Leu Xaa Val Xaa Ile Leu Xaa Val Xaa
1               5                   10

(2) INFORMATION FOR SEQ ID NO: 21:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:1
         (D) OTHER INFORMATION:/product= "bAla"

(ix) FEATURE:
         (A) NAME/KEY: Peptide
         (B) LOCATION:4
         (D) OTHER INFORMATION:/product= "OTHER"
             /note= "Asp(OBut)"

(ix) FEATURE:
         (A) NAME/KEY: Peptide
         (B) LOCATION:6
         (D) OTHER INFORMATION:/product= "OTHER"
             /note= "PIPERAZINYL-1-YL-ACETYL"
```

```
    (ix) FEATURE:
         (A) NAME/KEY: Peptide
         (B) LOCATION:7
         (D) OTHER INFORMATION:/product= "bAla"

(ix) FEATURE:
         (A) NAME/KEY: Peptide
         (B) LOCATION:10
         (D) OTHER INFORMATION:/product= "OTHER"
             /note= "Asp(OBut)"

(ix) FEATURE:
         (A) NAME/KEY: Peptide
         (B) LOCATION:12
         (D) OTHER INFORMATION:/product= "OTHER"
             /note= "PIPERAZINYL-1-YL-ACETIC ACID"

(xi) SEQUENCE DESCRIPTION: SEQ ID NO: 21:

Ala Ile Leu Xaa Val Xaa Ala Ile Leu Xaa Val Xaa
1               5                   10

(2) INFORMATION FOR SEQ ID NO: 22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION:1
         (D) OTHER INFORMATION:/product= "bAla"

(ix) FEATURE:
         (A) NAME/KEY: Peptide
         (B) LOCATION:4
         (D) OTHER INFORMATION:/product= "OTHER"
             /note= "Asp(OBut)"

(ix) FEATURE:
         (A) NAME/KEY: Peptide
         (B) LOCATION:6
         (D) OTHER INFORMATION:/product= "OTHER"
             /note= "PIPERAZINYL-1YL-ACETYL"

(ix) FEATURE:
         (A) NAME/KEY: Peptide
         (B) LOCATION:9
         (D) OTHER INFORMATION:/product= "OTHER"
             /note= "Asp(OBut)"

(ix) FEATURE:
         (A) NAME/KEY: Peptide
         (B) LOCATION:11
         (D) OTHER INFORMATION:/product= "OTHER"
             /note= "PIPERAZINYL-1-YL-ACETIC ACID"

(xi) SEQUENCE DESCRIPTION: SEQ ID NO: 22:

Ala Ile Leu Xaa Val Xaa Ile Leu Xaa Val Xaa
1               5                   10

(2) INFORMATION FOR SEQ ID NO: 23:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
```

```
          (A) NAME/KEY: Peptide
          (B) LOCATION:1
          (D) OTHER INFORMATION:/product= "OTHER"
              /note= "D-Leu"

(ix) FEATURE:
          (A) NAME/KEY: Peptide
          (B) LOCATION:5
          (D) OTHER INFORMATION:/product= "bAla"

(ix) FEATURE:
          (A) NAME/KEY: Peptide
          (B) LOCATION:6
          (D) OTHER INFORMATION:/product= "OTHER"
              /note= "D-Leu"

(ix) FEATURE:
          (A) NAME/KEY: Peptide
          (B) LOCATION:10
          (D) OTHER INFORMATION:/product= "bAla"

(xi) SEQUENCE DESCRIPTION: SEQ ID NO: 23:

Xaa Leu Asp Val Ala Xaa Leu Asp Val Ala
1               5                   10

(2) INFORMATION FOR SEQ ID NO: 24:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1
          (D) OTHER INFORMATION:/product= "OTHER"
              /note= "Asp(OBut)"

(ix) FEATURE:
          (A) NAME/KEY: Peptide
          (B) LOCATION:3
          (D) OTHER INFORMATION:/product= "OTHER"
              /note= "PIPERIDYL-5-ACETYL"

(xi) SEQUENCE DESCRIPTION: SEQ ID NO: 24:

Xaa Val Xaa Ile Leu
1               5

(2) INFORMATION FOR SEQ ID NO: 25:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1
          (D) OTHER INFORMATION:/product= "OTHER"
              /note= "D-Arg(Pbf) where Pbf is
              2,2,4,6,7-pentamethyl-dihydrobenzenefuran-5-sulphonyl"

(ix) FEATURE:
          (A) NAME/KEY: Peptide
          (B) LOCATION:2
          (D) OTHER INFORMATION:/product= "MeIle"

(ix) FEATURE:
          (A) NAME/KEY: Peptide
```

```
          (B) LOCATION:4
          (D) OTHER INFORMATION:/product= "OTHER"
              /note= "Asp(OBut)"

(ix) FEATURE:
          (A) NAME/KEY: Peptide
          (B) LOCATION:6
          (D) OTHER INFORMATION:/product= "OTHER"
              /note= "D-Arg(Pfb) where Pfb is
              2,2,4,6,7-pentamethyldihydrobenzenefuran-5-sulphonyl"

(ix) FEATURE:
          (A) NAME/KEY: Peptide
          (B) LOCATION:7
          (D) OTHER INFORMATION:/product= "MeIle"

(xi) SEQUENCE DESCRIPTION: SEQ ID NO: 25:

Xaa Ile Leu Xaa Val Xaa Ile Leu Asp Val
1               5                   10

(2) INFORMATION FOR SEQ ID NO: 26:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1
          (D) OTHER INFORMATION:/product= "OTHER"
              /note= "D-Arg(Pfb) Where Pfb is
              2,2,4,6,7-pentamethyldihydrobenzenefuran-5-sulphonyl"

(ix) FEATURE:
          (A) NAME/KEY: Peptide
          (B) LOCATION:2
          (D) OTHER INFORMATION:/product= "OTHER"
              /note= "D-Arg(Pfb) where Pfb is
              2,2,4,6,7-pentamethyldihydrobenzenefuran-5-sulphonyl"

(ix) FEATURE:
          (A) NAME/KEY: Peptide
          (B) LOCATION:3
          (D) OTHER INFORMATION:/product= "MeIle"

(ix) FEATURE:
          (A) NAME/KEY: Peptide
          (B) LOCATION:5
          (D) OTHER INFORMATION:/product= "OTHER"
              /note= "Asp(OBut)"

(ix) FEATURE:
          (A) NAME/KEY: Peptide
          (B) LOCATION:7
          (D) OTHER INFORMATION:/product= "OTHER"
              /note= "D-Arg(Pfb) where Pfb is
              2,2,4,6,7,-pentamethyldihydrobenzenefuran-5-sulphonyl"

(ix) FEATURE:
          (A) NAME/KEY: Peptide
          (B) LOCATION:8
          (D) OTHER INFORMATION:/product= "OTHER"
              /note= "D-Arg(Pfb) where Pfb is
              2,2,4,6,7-pentamethyldihydrobenzenefuran-5-sulphonyl"

(ix) FEATURE:
          (A) NAME/KEY: Peptide
          (B) LOCATION:9
          (D) OTHER INFORMATION:/product= "MeIle"

(xi) SEQUENCE DESCRIPTION: SEQ ID NO: 26:

Xaa Xaa Ile Leu Xaa Val Xaa Xaa Ile Leu Asp Val
```

(2) INFORMATION FOR SEQ ID NO: 27:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "D-Ala"

(ix) FEATURE:
        (A) NAME/KEY: Peptide
        (B) LOCATION:2
        (D) OTHER INFORMATION:/product= "OTHER"
            /note= "D-Ala"

(ix) FEATURE:
        (A) NAME/KEY: Peptide
        (B) LOCATION:3
        (D) OTHER INFORMATION:/product= "MeIle"

(ix) FEATURE:
        (A) NAME/KEY: Peptide
        (B) LOCATION:5
        (D) OTHER INFORMATION:/product= "OTHER"
            /note= "Asp(OBut)"

(ix) FEATURE:
        (A) NAME/KEY: Peptide
        (B) LOCATION:7
        (D) OTHER INFORMATION:/product= "OTHER"
            /note= "D-Arg(Pfb) where Pfb is
            2,2,4,6,7-pentamethyldihydrobenzenefuran-5-sulphonyl"

(ix) FEATURE:
        (A) NAME/KEY: Peptide
        (B) LOCATION:8
        (D) OTHER INFORMATION:/product= "OTHER"
            /note= "D-Arg(Pfb) where Pfb is
            2,2,4,6,7-pentamethyldihydrobenzenefuran-5-sulphonyl"

(ix) FEATURE:
        (A) NAME/KEY: Peptide
        (B) LOCATION:9
        (D) OTHER INFORMATION:/product= "MeIle"

(xi) SEQUENCE DESCRIPTION: SEQ ID NO: 27:

Xaa Xaa Ile Leu Xaa Val Xaa Xaa Ile Leu Asp Val
1               5                   10

(2) INFORMATION FOR SEQ ID NO: 28:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "MeIle"

(ix) FEATURE:
        (A) NAME/KEY: Peptide
        (B) LOCATION:3

```
        (D) OTHER INFORMATION:/product= "OTHER"
            /note= "Asp(OBut)"

(ix) FEATURE:
        (A) NAME/KEY: Peptide
        (B) LOCATION:5
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:6
        (D) OTHER INFORMATION:/product= "MeIle"

(ix) FEATURE:
        (A) NAME/KEY: Peptide
        (B) LOCATION:8
        (D) OTHER INFORMATION:/product= "OTHER"
            /note= "Asp(OBut)"

(ix) FEATURE:
        (A) NAME/KEY: Peptide
        (B) LOCATION:10
        (D) OTHER INFORMATION:/product= "OTHER"
            /note= "PIPERAZINYL-1-YL-ACETIC ACID"

(xi) SEQUENCE DESCRIPTION: SEQ ID NO: 28:

Ile Leu Xaa Val Xaa Ile Leu Xaa Val Xaa
1               5                   10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "MePhe"

(ix) FEATURE:
        (A) NAME/KEY: Peptide
        (B) LOCATION:3
        (D) OTHER INFORMATION:/product= "OTHER"
            /note= "Asp(OBut)"

(ix) FEATURE:
        (A) NAME/KEY: Peptide
        (B) LOCATION:5
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:6
        (D) OTHER INFORMATION:/product= "OTHER"
            /note= "MePhe"

(ix) FEATURE:
        (A) NAME/KEY: Peptide
        (B) LOCATION:8
        (D) OTHER INFORMATION:/product= "OTHER"
            /note= "Asp(OBut)"

(ix) FEATURE:
        (A) NAME/KEY: Peptide
        (B) LOCATION:10
        (D) OTHER INFORMATION:/product= "OTHER"
            /note= "PIPERAZINYL-1-YL-ACETIC ACID"

(xi) SEQUENCE DESCRIPTION: SEQ ID NO: 29:
```

```
Xaa Leu Xaa Val Xaa Xaa Leu Xaa Val Xaa
1               5                   10
```

(2) INFORMATION FOR SEQ ID NO: 30:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "D-Arg(Pfb) where Pfb is
            2,2,4,6,7-pentamethyldihydrobenzenefuran-5-sulphonyl"

(ix) FEATURE:
        (A) NAME/KEY: Peptide
        (B) LOCATION:2
        (D) OTHER INFORMATION:/product= "OTHER"
            /note= "MePhe"

(ix) FEATURE:
        (A) NAME/KEY: Peptide
        (B) LOCATION:4
        (D) OTHER INFORMATION:/product= "OTHER"
            /note= "Asp(OBut)"

(ix) FEATURE:
        (A) NAME/KEY: Peptide
        (B) LOCATION:6
        (D) OTHER INFORMATION:/product= "OTHER"
            /note= "PIPERAZINYL-1-YL-ACETYL"

(ix) FEATURE:
        (A) NAME/KEY: Peptide
        (B) LOCATION:7
        (D) OTHER INFORMATION:/product= "OTHER"
            /note= "D-Arg(Pfb) where Pfb is
            2,2,4,6,7-pentamethyldihydrobenzenefuran-5-sulphonyl"

(ix) FEATURE:
        (A) NAME/KEY: Peptide
        (B) LOCATION:8
        (D) OTHER INFORMATION:/product= "OTHER"
            /note= "MePhe"

(ix) FEATURE:
        (A) NAME/KEY: Peptide
        (B) LOCATION:10
        (D) OTHER INFORMATION:/product= "OTHER"
            /note= "Asp(OBut)"

(ix) FEATURE:
        (A) NAME/KEY: Peptide
        (B) LOCATION:12
        (D) OTHER INFORMATION:/product= "OTHER"
            /note= "PIPERAZINYL-1-YL-ACETIC ACID"

(xi) SEQUENCE DESCRIPTION: SEQ ID NO: 30:

```
Xaa Xaa Leu Xaa Val Xaa Xaa Xaa Leu Xaa Val Xaa
1               5                   10
```

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "MeIle"

(ix) FEATURE:
            (A) NAME/KEY: Peptide
            (B) LOCATION:3
            (D) OTHER INFORMATION:/product= "OTHER"
                /note= "Asp(OBut)"

(ix) FEATURE:
            (A) NAME/KEY: Peptide
            (B) LOCATION:5
            (D) OTHER INFORMATION:/product= "OTHER"
                /note= "1,4,-DIAZEPAN-1-YL-ACETYL"

(ix) FEATURE:
            (A) NAME/KEY: Peptide
            (B) LOCATION:6
            (D) OTHER INFORMATION:/product= "MeIle"

(ix) FEATURE:
            (A) NAME/KEY: Peptide
            (B) LOCATION:8
            (D) OTHER INFORMATION:/product= "OTHER"
                /note= "Asp(OBut)"

(ix) FEATURE:
            (A) NAME/KEY: Peptide
            (B) LOCATION:10
            (D) OTHER INFORMATION:/product= "OTHER"
                /note= "1,4-DIAZEPAN-1-YL-ACETIC ACID"

(xi) SEQUENCE DESCRIPTION: SEQ ID NO: 31:

Ile Leu Xaa Val Xaa Ile Leu Xaa Val Xaa
1               5                   10

(2) INFORMATION FOR SEQ ID NO: 32:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "NH2-(CH2)2-S-CH2-CO-MeIle"

(ix) FEATURE:
            (A) NAME/KEY: Peptide
            (B) LOCATION:3
            (D) OTHER INFORMATION:/product= "OTHER"
                /note= "Asp(OBut)"

(ix) FEATURE:
            (A) NAME/KEY: Peptide
            (B) LOCATION:5
            (D) OTHER INFORMATION:/product= "OTHER"
                /note= "NH-(CH2)2-S-CH2-CO-"

(ix) FEATURE:
            (A) NAME/KEY: Peptide
            (B) LOCATION:6
            (D) OTHER INFORMATION:/product= "MeIle"

(ix) FEATURE:
            (A) NAME/KEY: Peptide
            (B) LOCATION:8
            (D) OTHER INFORMATION:/product= "OTHER"

/note= "Asp(OBut)"

(xi) SEQUENCE DESCRIPTION: SEQ ID NO: 32:

Xaa Leu Xaa Val Xaa Ile Leu Xaa Val
1               5

(2) INFORMATION FOR SEQ ID NO: 33:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "D-Ala"

(ix) FEATURE:
        (A) NAME/KEY: Peptide
        (B) LOCATION:2
        (D) OTHER INFORMATION:/product= "OTHER"
            /note= "D-Arg(Pfb) where Pfb is
            2,2,4,6,7-pentamethyldihydrobenzenefuran-5-sulphonyl"

(ix) FEATURE:
        (A) NAME/KEY: Peptide
        (B) LOCATION:3
        (D) OTHER INFORMATION:/product= "MeIle"

(ix) FEATURE:
        (A) NAME/KEY: Peptide
        (B) LOCATION:5
        (D) OTHER INFORMATION:/product= "OTHER"
            /note= "Asp(OBut)"

(ix) FEATURE:
        (A) NAME/KEY: Peptide
        (B) LOCATION:7
        (D) OTHER INFORMATION:/product= "OTHER"
            /note= "D-Ala"

(ix) FEATURE:
        (A) NAME/KEY: Peptide
        (B) LOCATION:8
        (D) OTHER INFORMATION:/product= "OTHER"
            /note= "D-Arg(Pfb) where Pfb is
            2,2,4,6,7-pentamethyldihydrobenzenefuran-5-sulphonyl"

(ix) FEATURE:
        (A) NAME/KEY: Peptide
        (B) LOCATION:9
        (D) OTHER INFORMATION:/product= "MeIle"

(ix) FEATURE:
        (A) NAME/KEY: Peptide
        (B) LOCATION:11
        (D) OTHER INFORMATION:/product= "OTHER"
            /note= "Asp(OBut)"

(xi) SEQUENCE DESCRIPTION: SEQ ID NO: 33:

Xaa Xaa Ile Leu Xaa Val Xaa Xaa Ile Leu Xaa Val
1               5                   10